US011085924B2

(12) United States Patent
Floch

(10) Patent No.: US 11,085,924 B2
(45) Date of Patent: Aug. 10, 2021

(54) COMPOSITIONS AND METHODS FOR ASSESSING THE RISK OF CANCER OCCURRENCE

(71) Applicant: Syncerus S.A R.L., Luxembourg (LU)

(72) Inventor: Jean-Francois Floch, Garlan (FR)

(73) Assignee: Syncerus S.À. R.L., Luxembourg (LU)

( * ) Notice: Subject to any disclaimer, the term of this patent is extended or adjusted under 35 U.S.C. 154(b) by 214 days.

(21) Appl. No.: 16/067,162

(22) PCT Filed: Jan. 2, 2017

(86) PCT No.: PCT/EP2017/050034
§ 371 (c)(1),
(2) Date: Jun. 29, 2018

(87) PCT Pub. No.: WO2017/114973
PCT Pub. Date: Jul. 6, 2017

(65) Prior Publication Data
US 2019/0011452 A1    Jan. 10, 2019

(30) Foreign Application Priority Data

Dec. 31, 2015 (EP) .................................... 15307190
Feb. 5, 2016 (EP) .................................... 16305133

(51) Int. Cl.
| | |
|---|---|
| *G01N 33/574* | (2006.01) |
| *G01N 33/74* | (2006.01) |
| *C07K 16/30* | (2006.01) |
| *C07K 16/26* | (2006.01) |

(52) U.S. Cl.
CPC ....... *G01N 33/57496* (2013.01); *C07K 16/26* (2013.01); *C07K 16/30* (2013.01); *G01N 33/57419* (2013.01); *G01N 33/57438* (2013.01); *G01N 33/57446* (2013.01); *G01N 33/57449* (2013.01); *G01N 33/74* (2013.01); *G01N 2333/595* (2013.01); *G01N 2800/50* (2013.01)

(58) Field of Classification Search
None
See application file for complete search history.

(56) References Cited

U.S. PATENT DOCUMENTS

| 4,444,887 A | 4/1984 | Hoffmann |
| 4,716,111 A | 12/1987 | Osband et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,814,318 A | 9/1998 | Lonberg et al. |
| 2011/0229488 A1* | 9/2011 | Floch ............... G01N 33/57438 424/158.1 |

FOREIGN PATENT DOCUMENTS

| EP | 0 239 400 | 9/1987 |
| EP | 0 519 596 | 12/1992 |
| EP | 0 592 106 | 4/1994 |
| WO | WO 91/09967 | 7/1991 |
| WO | WO 91/10741 | 7/1991 |
| WO | WO 96/33735 | 10/1996 |
| WO | WO 96/34096 | 10/1996 |
| WO | WO 98/16654 | 4/1998 |
| WO | WO 98/24893 | 6/1998 |
| WO | WO 98/46645 | 10/1998 |
| WO | WO 98/50433 | 11/1998 |
| WO | WO 2006/032980 | 3/2006 |
| WO | WO 2011/083088 | 7/2011 |
| WO | WO 2011/083089 | 7/2011 |
| WO | WO 2011/083090 | 7/2011 |
| WO | WO 2011/083091 | 7/2011 |
| WO | WO 2011/116954 | 9/2011 |
| WO | WO 2012/013609 | 2/2012 |
| WO | WO 2012/164035 | 12/2012 |

OTHER PUBLICATIONS

Ausubel et al., Current Protocols in Molecular Biology (1987).
Do et al., *A New Biomarker that Predicts Colonic Neoplasia Outcome in Patients with Hyperplastic Colonic Polyps*, 5(4) Cancer Prev. Res. 655-684 (2012).
Jones et al., *Replacing the complementarity-determining regions in human antibody with those from a mouse*, 321 Nature 522-525 (May 29, 1986).
Padlan, *A Possible Procedure for Reducing the Immunogenicity of Antibody Variable Domains While Preserving Their Ligand-Binding Properties*, 28(4/5) Molecular Immunology 489-498 (1991).
Roguska et al., *Humanization of murine monoclonal antibodies through variable domain resurfacing*, 91 Proc. Natl. Acad. Sci. 969-973 (Feb. 1994).
Singh et al., *Progastrin Peptides Increase the Risk of Developing Colonic Tumors: Impact on Colonic Stem Cells*, 8 Curr. Colorectal Cancer Rep. 277-289 (2012).
Studnicka et al., *Human-engineered monoclonal antibodies retain full specific biding activity by preserving non-CDR complementarity-modulating residues*, 7(6) Protein Engineering Design & Selection 805-814 (Jun. 1, 1994) (abstract only).

* cited by examiner

*Primary Examiner* — Andrea S Grossman
(74) *Attorney, Agent, or Firm* — Panitch Schwarze Belisario & Nadel LLP

(57) ABSTRACT

The present invention provides a method for evaluating the risk of occurrence of cancer in an individual.

Figure 1:
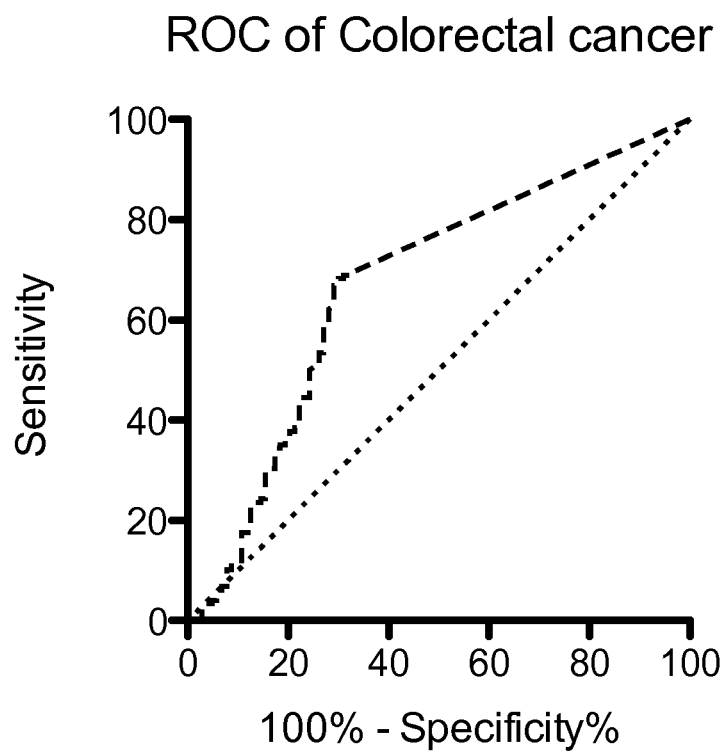

3 Claims, 15 Drawing Sheets
Specification includes a Sequence Listing.

| | Results |
|---|---|
| Area | 0.6694 |
| Std. Error | 0.03583 |
| 95% confidence interval | 0.5992 to 0.7396 |
| P value | < 0.0001 |
| Data | |
| Controls (control n=103) | 103 |
| Patients (CRC n=148) | 148 |

| | Results |
|---|---|
| Area | 0.8564 |
| Std. Error | 0.03138 |
| 95% confidence interval | 0.7949 to 0.9180 |
| P value | < 0.0001 |
| Data | |
| Controls (control n=103) | 103 |
| Patients (hepatocellular =47) | 47 |

| | Results |
|---|---|
| Area | 0.6782 |
| Std. Error | 0.04704 |
| 95% confidence interval | 0.5860 to 0.7704 |
| P value | 0.0006417 |
| Data | |
| Controls (control n=103) | 103 |
| Patients (pancreatic cancer n=44) | 44 |

| | Results |
|---|---|
| Area under the ROC curve | |
| Area | 0.5965 |
| Std. Error | 0.09156 |
| 95% confidence interval | 0.4170 to 0.7760 |
| P value | 0.3647 |
| Data | |
| Controls (control n=103) | 103 |
| Patients (ovarian n=8) | 8 |

Median: 0.00 8.45

|  | Number of samples | Median |
|---|---|---|
| control | 322 | 0.000 |
| sarcoma | 4 | 2.750 |
| breast | 65 | 4.000 |
| pancreas | 6 | 4.150 |
| endometrium | 5 | 4.300 |
| hodgkin lymphoma | 4 | 4.350 |
| cervix utery | 25 | 5.300 |
| colorectal | 52 | 5.900 |
| melanoma of skin | 46 | 6.450 |
| NMSC | 9 | 7.400 |
| stomach | 4 | 7.400 |
| ovarian | 8 | 9.250 |
| liver | 3 | 21.50 |

```
                        SEQUENCE LISTING

<160> NUMBER OF SEQ ID NOS: 40

<210> SEQ ID NO 1
<211> LENGTH: 80
<212> TYPE: PRT
<213> ORGANISM: Homo sapiens
<220> FEATURE:
<221> NAME/KEY: SITE
<222> LOCATION: (1)..(80)
<223> OTHER INFORMATION: Human progastrin

<400> SEQUENCE: 1

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 2
<211> LENGTH: 14
<212> TYPE: PRT
<213> ORGANISM: Artificial
<220> FEATURE:
<223> OTHER INFORMATION: Amino acids 1-14, N-terminal extremity of human
      progastrin

<400> SEQUENCE: 2

Ser Trp Lys Pro Arg Ser Gln Gln Pro Asp Ala Pro Leu Gly
1               5                   10

<210> SEQ ID NO 3
<211> LENGTH: 26
<212> TYPE: PRT
<213> ORGANISM: Artificial
<220> FEATURE:
<223> OTHER INFORMATION: Amino acids 55-80, C-terminal extremity of
      human progastrin

<400> SEQUENCE: 3
```

```
Gln Gly Pro Trp Leu Glu Glu Glu Glu Ala Tyr Gly Trp Met Asp
 1               5                  10                  15

Phe Gly Arg Arg Ser Ala Glu Asp Glu Asn
            20                  25

<210> SEQ ID NO 4
<211> LENGTH: 8
<212> TYPE: PRT
<213> ORGANISM: Artificial
<220> FEATURE:
<223> OTHER INFORMATION: 6B5B11C10 CDR-H1

<400> SEQUENCE: 4

Gly Tyr Ile Phe Thr Ser Tyr Trp
 1               5

<210> SEQ ID NO 5
<211> LENGTH: 8
<212> TYPE: PRT
<213> ORGANISM: Artificial
<220> FEATURE:
<223> OTHER INFORMATION: 6B5B11C10 CDR-H2

<400> SEQUENCE: 5

Phe Tyr Pro Gly Asn Ser Asp Ser
 1               5

<210> SEQ ID NO 6
<211> LENGTH: 8
<212> TYPE: PRT
<213> ORGANISM: Artificial
<220> FEATURE:
<223> OTHER INFORMATION: 6B5B11C10 CDR-H3

<400> SEQUENCE: 6

Thr Arg Arg Asp Ser Pro Gln Tyr
 1               5

<210> SEQ ID NO 7
<211> LENGTH: 11
<212> TYPE: PRT
<213> ORGANISM: Artificial
<220> FEATURE:
<223> OTHER INFORMATION: 6B5B11C10 CDR-L1

<400> SEQUENCE: 7

Gln Ser Ile Val His Ser Asn Gly Asn Thr Tyr
 1               5                  10

<210> SEQ ID NO 8
<211> LENGTH: 3
<212> TYPE: PRT
<213> ORGANISM: Artificial
<220> FEATURE:
<223> OTHER INFORMATION: 6B5B11C10 CDR-L2

<400> SEQUENCE: 8

Lys Val Ser
 1

<210> SEQ ID NO 9
<211> LENGTH: 9
<212> TYPE: PRT
<213> ORGANISM: Artificial
<220> FEATURE:
<223> OTHER INFORMATION: 6B5B11C10 CDR-L3
```

```
<400> SEQUENCE: 9

Phe Gln Gly Ser His Val Pro Phe Thr
1               5

<210> SEQ ID NO 10
<211> LENGTH: 7
<212> TYPE: PRT
<213> ORGANISM: Artificial
<220> FEATURE:
<223> OTHER INFORMATION: 20D2C3G2 CDR-H1

<400> SEQUENCE: 10

Gly Tyr Thr Phe Ser Ser Trp
1               5

<210> SEQ ID NO 11
<211> LENGTH: 8
<212> TYPE: PRT
<213> ORGANISM: Artificial
<220> FEATURE:
<223> OTHER INFORMATION: 20D2C3G2 CDR-H2

<400> SEQUENCE: 11

Phe Leu Pro Gly Ser Gly Ser Thr
1               5

<210> SEQ ID NO 12
<211> LENGTH: 11
<212> TYPE: PRT
<213> ORGANISM: Artificial
<220> FEATURE:
<223> OTHER INFORMATION: 20D2C3G2 CDR-H3

<400> SEQUENCE: 12

Ala Thr Asp Gly Asn Tyr Asp Trp Phe Ala Tyr
1               5                   10

<210> SEQ ID NO 13
<211> LENGTH: 11
<212> TYPE: PRT
<213> ORGANISM: Artificial
<220> FEATURE:
<223> OTHER INFORMATION: 20D2C3G2 CDR-L1

<400> SEQUENCE: 13

Gln Ser Leu Val His Ser Ser Gly Val Thr Tyr
1               5                   10

<210> SEQ ID NO 14
<211> LENGTH: 3
<212> TYPE: PRT
<213> ORGANISM: Artificial
<220> FEATURE:
<223> OTHER INFORMATION: 20D2C3G2 CDR-L2

<400> SEQUENCE: 14

Lys Val Ser
1

<210> SEQ ID NO 15
<211> LENGTH: 9
<212> TYPE: PRT
<213> ORGANISM: Artificial
<220> FEATURE:
<223> OTHER INFORMATION: 20D2C3G2 CDR-L3

<400> SEQUENCE: 15
```

Ser Gln Ser Thr His Val Pro Pro Thr
1               5

<210> SEQ ID NO 16
<211> LENGTH: 8
<212> TYPE: PRT
<213> ORGANISM: Artificial
<220> FEATURE:
<223> OTHER INFORMATION: 1E9D9B6 CDR-H1

<400> SEQUENCE: 16

Gly Tyr Thr Phe Thr Ser Tyr Tyr
1               5

<210> SEQ ID NO 17
<211> LENGTH: 8
<212> TYPE: PRT
<213> ORGANISM: Artificial
<220> FEATURE:
<223> OTHER INFORMATION: 1E9D9B6 CDR-H2

<400> SEQUENCE: 17

Ile Asn Pro Ser Asn Gly Gly Thr
1               5

<210> SEQ ID NO 18
<211> LENGTH: 10
<212> TYPE: PRT
<213> ORGANISM: Artificial
<220> FEATURE:
<223> OTHER INFORMATION: 1E9D9B6 CDR-H3

<400> SEQUENCE: 18

Thr Arg Gly Gly Tyr Tyr Pro Phe Asp Tyr
1               5                   10

<210> SEQ ID NO 19
<211> LENGTH: 11
<212> TYPE: PRT
<213> ORGANISM: Artificial
<220> FEATURE:
<223> OTHER INFORMATION: 1E9D9B6 CDR-L1

<400> SEQUENCE: 19

Gln Ser Leu Leu Asp Ser Asp Gly Lys Thr Tyr
1               5                   10

<210> SEQ ID NO 20
<211> LENGTH: 3
<212> TYPE: PRT
<213> ORGANISM: Artificial
<220> FEATURE:
<223> OTHER INFORMATION: 1E9D9B6 CDR-L2

<400> SEQUENCE: 20

Leu Val Ser
1

<210> SEQ ID NO 21
<211> LENGTH: 9
<212> TYPE: PRT
<213> ORGANISM: Artificial
<220> FEATURE:
<223> OTHER INFORMATION: 1E9D9B6 CDR-L3

<400> SEQUENCE: 21

Trp Gln Gly Thr His Ser Pro Tyr Thr
1               5

<210> SEQ ID NO 22
<211> LENGTH: 9
<212> TYPE: PRT
<213> ORGANISM: Artificial
<220> FEATURE:
<223> OTHER INFORMATION: 1B3B4F11 CDR-H1

<400> SEQUENCE: 22

Gly Tyr Ser Ile Thr Ser Asp Tyr Ala
1               5

<210> SEQ ID NO 23
<211> LENGTH: 7
<212> TYPE: PRT
<213> ORGANISM: Artificial
<220> FEATURE:
<223> OTHER INFORMATION: 1B3B4F11 CDR-H2

<400> SEQUENCE: 23

Ile Ser Phe Ser Gly Tyr Thr
1               5

<210> SEQ ID NO 24
<211> LENGTH: 14
<212> TYPE: PRT
<213> ORGANISM: Artificial
<220> FEATURE:
<223> OTHER INFORMATION: 1B3B4F11 CDR-H3

<400> SEQUENCE: 24

Ala Arg Glu Val Asn Tyr Gly Asp Ser Tyr His Phe Asp Tyr
1               5                   10

<210> SEQ ID NO 25
<211> LENGTH: 7
<212> TYPE: PRT
<213> ORGANISM: Artificial
<220> FEATURE:
<223> OTHER INFORMATION: 1B3B4F11 CDR-L1

<400> SEQUENCE: 25

Ser Gln His Arg Thr Tyr Thr
1               5

<210> SEQ ID NO 26
<211> LENGTH: 7
<212> TYPE: PRT
<213> ORGANISM: Artificial
<220> FEATURE:
<223> OTHER INFORMATION: 1B3B4F11 CDR-L2

<400> SEQUENCE: 26

Val Lys Lys Asp Gly Ser His
1               5

<210> SEQ ID NO 27
<211> LENGTH: 13
<212> TYPE: PRT
<213> ORGANISM: Artificial
<220> FEATURE:
<223> OTHER INFORMATION: 1B3B4F11 CDR-L3

<400> SEQUENCE: 27

Gly Val Gly Asp Ala Ile Lys Gly Gln Ser Val Phe Val

-continued

```
                1               5                   10

<210> SEQ ID NO 28
<211> LENGTH: 8
<212> TYPE: PRT
<213> ORGANISM: Artificial
<220> FEATURE:
<223> OTHER INFORMATION: 1C10D3B9 CDR-H1

<400> SEQUENCE: 28

Gly Phe Thr Phe Thr Thr Tyr Ala
1               5

<210> SEQ ID NO 29
<211> LENGTH: 8
<212> TYPE: PRT
<213> ORGANISM: Artificial
<220> FEATURE:
<223> OTHER INFORMATION: 1C10D3B9 CDR-H2

<400> SEQUENCE: 29

Ile Ser Ser Gly Gly Thr Tyr Thr
1               5

<210> SEQ ID NO 30
<211> LENGTH: 10
<212> TYPE: PRT
<213> ORGANISM: Artificial
<220> FEATURE:
<223> OTHER INFORMATION: 1C10D3B9 CDR-H3

<400> SEQUENCE: 30

Ala Thr Gln Gly Asn Tyr Ser Leu Asp Phe
1               5                   10

<210> SEQ ID NO 31
<211> LENGTH: 11
<212> TYPE: PRT
<213> ORGANISM: Artificial
<220> FEATURE:
<223> OTHER INFORMATION: 1C10D3B9 CDR-L1

<400> SEQUENCE: 31

Lys Ser Leu Arg His Thr Lys Gly Ile Thr Phe
1               5                   10

<210> SEQ ID NO 32
<211> LENGTH: 3
<212> TYPE: PRT
<213> ORGANISM: Artificial
<220> FEATURE:
<223> OTHER INFORMATION: 1C10D3B9 CDR-L2

<400> SEQUENCE: 32

Gln Met Ser
1

<210> SEQ ID NO 33
<211> LENGTH: 9
<212> TYPE: PRT
<213> ORGANISM: Artificial
<220> FEATURE:
<223> OTHER INFORMATION: 1C10D3B9 CDR-L3

<400> SEQUENCE: 33

Ala Gln Asn Leu Glu Leu Pro Leu Thr
1               5
```

```
<210> SEQ ID NO 34
<211> LENGTH: 8
<212> TYPE: PRT
<213> ORGANISM: Artificial
<220> FEATURE:
<223> OTHER INFORMATION: 2C6C3C7 CDR-H1

<400> SEQUENCE: 34

Gly Phe Ile Phe Ser Ser Tyr Gly
1               5

<210> SEQ ID NO 35
<211> LENGTH: 8
<212> TYPE: PRT
<213> ORGANISM: Artificial
<220> FEATURE:
<223> OTHER INFORMATION: 2C6C3C7 CDR-H2

<400> SEQUENCE: 35

Ile Asn Thr Phe Gly Asp Arg Thr
1               5

<210> SEQ ID NO 36
<211> LENGTH: 7
<212> TYPE: PRT
<213> ORGANISM: Artificial
<220> FEATURE:
<223> OTHER INFORMATION: 2C6C3C7 CDR-H3

<400> SEQUENCE: 36

Ala Arg Gly Thr Gly Thr Tyr
1               5

<210> SEQ ID NO 37
<211> LENGTH: 11
<212> TYPE: PRT
<213> ORGANISM: Artificial
<220> FEATURE:
<223> OTHER INFORMATION: 2C6C3C7 CDR-L1

<400> SEQUENCE: 37

Gln Ser Leu Leu Asp Ser Asp Gly Lys Thr Tyr
1               5                   10

<210> SEQ ID NO 38
<211> LENGTH: 3
<212> TYPE: PRT
<213> ORGANISM: Artificial
<220> FEATURE:
<223> OTHER INFORMATION: 2C6C3C7 CDR-L2

<400> SEQUENCE: 38

Leu Val Ser
1

<210> SEQ ID NO 39
<211> LENGTH: 9
<212> TYPE: PRT
<213> ORGANISM: Artificial
<220> FEATURE:
<223> OTHER INFORMATION: 2C6C3C7 CDR-L3

<400> SEQUENCE: 39

Trp Gln Gly Thr His Phe Pro Gln Thr
1               5
```

```
<210> SEQ ID NO 40
<211> LENGTH: 10
<212> TYPE: PRT
<213> ORGANISM: Artificial
<220> FEATURE:
<223> OTHER INFORMATION: Amino acids 71-80 of progastrin

<400> SEQUENCE: 40

Phe Gly Arg Arg Ser Ala Glu Asp Glu Asn
1               5                   10
```

COMPOSITIONS AND METHODS FOR ASSESSING THE RISK OF CANCER OCCURRENCE

CROSS-REFERENCE TO RELATED APPLICATIONS

This application is a U.S. National Stage Application pursuant to 35 U.S.C. § 371 of International Patent Application PCT/EP2017/050034, filed on Jan. 2, 2017, and published as WO 2017/114973 on Jul. 6, 2017, which claims priority to European Patent Application 16305133.7, filed on Feb. 5, 2016, and European Patent Application 15307190.7, filed on Dec. 31, 2015, all of which are incorporated herein by reference in their entireties for all purposes.

INTRODUCTION

Cancer is a multi-faceted disease in which a group of cells display uncontrolled growth, invasion that intrudes upon and destroys adjacent tissues, and sometimes metastasis, or spreading to other locations in the body via lymph or blood. These three malignant properties of cancers differentiate them from benign tumors, which do not invade or metastasize.

There are a number of methods currently used to treat each type of cancer, including surgery, radiotherapy, chemotherapy and targeted therapy. Successful cancer therapy is directed to the primary tumor and to any metastases, whether clinically apparent or microscopic.

The selection of an appropriate treatment is crucial for the patient. It is essential to know when to use immediately a heavy and aggressive treatment protocol in order to prevent extension of an aggressive cancer. In contrast, performing a heavy and aggressive treatment when it is not necessitated by the tumor carried by the patient is also disadvantageous for the patient. Indeed, heavy and aggressive treatments always lead to adverse toxicities that may significantly affect the patient's quality of life. For example most of them are mutagenic and are thus prone to induce secondary tumors. In addition, such heavy and aggressive treatments are usually very costly, and should thus be performed only when it is necessary.

Currently, treatment selection for solid tumors is based on tumor staging, which is usually performed using the Tumor/Node/Metastasis (TNM) test from the American Joint Committee on Cancer (AJCC). The TNM system assigns a number based on three categories. "T" denotes the tumor size, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome.

It is commonly acknowledged that, while this test and staging system provides some valuable information concerning the stage at which solid cancer has been diagnosed in the patient, it is imprecise and insufficient. In particular, it is limited to solid tumors. Liquid tumors on the other hand are mostly characterized by the identification of cytogenetic alterations.

Most importantly, the TNM test fails to identify the earliest stages of tumor progression. These early stages offer the most promising window for therapy. Detection of a cancer at the very beginning of its development allows targeted, efficient therapy, with reduced side-effects. It is thus important to identify patients at the earliest possible stage as a part of a screening of the whole population. Cancer can thus be identified in a community early, enabling earlier intervention and management to reduce mortality and suffering from said disease. There is a real need for better prognosis tests of the occurrence of cancer, not only to improve patient global survival, but also to improve their quality of life and to keep aggressive and costly chemotherapies for patients who will really benefit from them. In particular, there is a need for a test assessing the risk of a subject to develop a cancer.

DESCRIPTION

The present invention provides a simple and efficient method for prognosing the occurrence of a cancer in subjects who have never been previously diagnosed with cancer. The present inventors have shown that the presence of progastrin in sample of a subject is a good and reliable indication of whether said subject will develop cancer. This relation is independent of age or any other parameter. Progastrin thus offers a simple and efficient tool for determining the risks of a subject of developing a cancer. Progastrin is thus a marker of the earliest stages of cancer.

Prognosis tests based on progastrin levels have been described previously. However, such tests are limited to predicting the risk of a patient having hyperplastic polyp, of developing a colonic neoplasia after resection of said hyperplastic polyps (WO 2012/164035; Do et al., Cancer Prev Res, 5(4): 675-684, 2012). Such tests are thus of a limited use, since they are restricted to prognosing a cancer which is already known to be present. They cannot be used to evaluate the risk of a subject who does not have any sign of cancer of developing this disease.

In a first aspect, the invention relates to a method of evaluating the risk of the occurrence of a cancer in a subject who has not been previously diagnosed with cancer, said method comprising steps of:
a) determining the level of progastrin in sample of said subject;
b) determining the risk that said subject will develop a cancer based on the level of step a).

A ROC (Receiver Operating Characteristic) analysis of clinical data has shown that the presence of progastrin is a highly specific and sensitive marker. Progastrin is essentially not detectable in samples of subjects who do not develop cancer. On the other hand, a subject who has never been diagnosed with cancer has a non-negligible risk of developing a cancer in the future if progastrin is detectable in his/her sample.

The method of the invention makes it possible to evaluate easily and reliably the risk of a subject who has not been previously diagnosed with cancer to develop cancer. In other words, this method also enables the identification of subjects who will develop cancer, even though they presently display no symptom. Such patients already have cancer, even though they perceive no symptom thereof.

The expression "evaluation of a risk of development of a cancer in a subject" designates the determination of a relative probability for a given subject to display symptoms of cancer in the future. A method according to the invention represents a tool in the evaluation of said risk, in combination with other methods or indicators such as clinical examination, biopsy and determination of the level of a known biomarker of cancer, such as, for example, CA125 and/or OVA1.

A "subject" which may be subjected to the methodology described herein may be any of mammalian animals including human, dog, cat, cattle, goat, pig, swine, sheep and monkey. A human subject can be known as a "patient". Preferably, a "subject" is a mammal that is not suffering from cancer and is not suspected of suffering from cancer and has not been diagnosed with cancer. As used herein, a "subject suffering from cancer" refers to a mammal that is suffering from cancer and shows symptoms thereof, or has been diagnosed with cancer. A subject has been "diagnosed with cancer" when a medical test conducted by a medical practitioner has revealed the presence of cancer. As used herein, a "symptom" is any subjective evidence of disease, e.g., cancer. A "symptom" is a departure from normal function or feeling which is noticed by a patient, reflecting the presence of an unusual state, or of a disease, e.g., cancer. A disease is considered asymptomatic if a patient is a carrier for said disease, but experiences no symptom. Asymptomatic conditions may not be discovered until the patient undergoes medical tests, such as, e.g., measuring the progastrin level.

The present method is also particularly useful because it allows one to identify a cancer in a subject, even when the subject has never been diagnosed with cancer and/or does not experience any symptom thereof. Progastrin is a highly specific and sensitive cancer marker. The detection of progastrin in a subject indicates that there is a high likelihood that said subject will develop a cancer. Progastrin is thus a particularly important biomarker for identifying subjects who will develop cancer, even though they do not display any symptoms yet. The invention is particularly advantageous because it allows screening a population of subjects seemingly healthy, i.e., who have never been diagnosed with cancer and/or have not experienced any symptom thereof, and identifying those who will develop cancer. By "screening" it is herein referred to a method used to identify within a population the possible presence of an as-yet-undiagnosed disease in individuals without signs or symptoms. This can include individuals with pre-symptomatic or unrecognized symptomatic disease. It will be clear to the skilled person that as such, screening tests are somewhat unique in that they are performed on persons apparently in good health. The proximate goal of cancer screening is the identification of early stage cancer, or precancerous lesions, before a person develops symptoms and at a point in the disease trajectory when treatment is likely to result in cure.

In another aspect, the invention provides a method of prognosing a cancer in a subject who has not been previously diagnosed with cancer, said method comprising the steps of:
a) determining the level of progastrin in sample of said subject;
b) prognosing a cancer based on the level of step a).

"Prognosis" as used herein means the likelihood of recovery from a disease or the prediction of the probable development or outcome of a disease. For example, if a sample from a subject is negative for the presence of progastrin, then the "prognosis" for that subject is better than if the sample is positive for progastrin.

By "progastrin", it is herein referred to the mammalian progastrin peptide. Progastrin is formed by cleavage of the first 21 amino acids (the signal peptide) from preprogastrin, a 101 amino acids peptide (Amino acid sequence reference: AAB19304.1) which is the primary translation product of the gastrin gene. The 80 amino acid chain of progastrin is further processed by cleavage and modifying enzymes to several biologically active gastrin hormone forms: gastrin 34 (G34) and glycine-extended gastrin 34 (G34-Gly), comprising amino acids 38-71 of progastrin, gastrin 17 (G17) and glycine-extended gastrin 17 (G17-Gly), comprising amino acids 55 to 71 of progastrin.

In a preferred embodiment, the progastrin peptide of the invention is human progastrin. More preferably, the expression "human progastrin" refers to the human PG of sequence SEQ ID No. 1. Human progastrin comprises notably a N-terminus and a C-terminus domains which are not present in the biologically active gastrin hormone forms mentioned above. Preferably, the sequence of said N-terminus domain is represented by SEQ ID NO. 2. In another preferred embodiment, the sequence of said C-terminus domain is represented by SEQ ID NO. 3.

The present invention provides methods for detection of progastrin in samples, especially of biological samples such as biological fluids and cells, tissues, biopsy samples and organ sections etc.

By "biological sample" it is herein referred to any sample that may be taken from a subject. Such a sample must allow for the determination of the expression levels of progastrin. Progastrin is known to be a secreted protein. Preferred biological samples for the determination of the level of the progastrin protein thus include biological fluids. A "biological fluid" as used herein means any fluid that includes material of biological origin. Preferred biological fluids for use in the present invention include bodily fluids of an animal, e.g. a mammal, preferably a human subject. The bodily fluid may be any bodily fluid, including but not limited to blood, plasma, serum, lymph, cerebrospinal fluid (CSF), saliva, sweat and urine. Preferably, said preferred liquid biological samples include samples such as a blood sample, a plasma sample, or a lymph sample. More preferably, the biological sample is a blood sample. Indeed, such a blood sample may be obtained by a completely harmless blood collection from the patient and thus allows for a non-invasive assessment of the risks that the subject will develop a tumor.

A "biological sample" as used herein also includes a solid cancer sample of the patient to be tested, when the cancer is a solid cancer. Such solid cancer sample allows the skilled person to perform any type of measurement of the level of the biomarker of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non tumor healthy tissue. The "cancer sample" should thus be limited to tumor tissue taken from the patient. Said "cancer sample" may be a biopsy sample or a sample taken from a surgical resection therapy.

According to one aspect, the sample from the patient is a cancer cell or a cancer tissue.

This sample may be taken and if necessary prepared according to methods known to a person skilled in the art. In particular, it is well known in the art that the sample should be taken from a fasting subject.

The cancer cell or cancer tissue in the present invention is not particularly limited.

As used herein, the term "cancer" refers to or describes the physiological condition in mammals that is typically characterized by unregulated cell proliferation. The terms "cancer" and "cancerous" as used herein are meant to encompass all stages of the disease. A "cancer" as used herein is any malignant neoplasm resulting from the undesired growth, the invasion, and under certain conditions metastasis of impaired cells in an organism. The cells giving rise to cancer are genetically impaired and have usually lost their ability to control cell division, cell migration behavior, differentiation status and/or cell death machinery. Most cancers form a tumor but some hematopoietic cancers, such as leukemia, do not.

Thus, a "cancer" as used herein may include both benign and malignant cancers. Examples of cancer include but are not limited to, carcinoma, lymphoma, blastoma, sarcoma, and leukaemia or lymphoid malignancies. More specifically, a cancer according to the present invention is selected from the group comprising squamous cell cancer (e.g., epithelial squamous cell cancer), lung cancer including small-cell lung cancer, non-small cell lung cancer, adenocarcinoma of the lung and squamous carcinoma of the lung, oropharyngeal cancer, nasopharyngeal cancer, laryngeal cancer, cancer of the peritoneum, oesophageal cancer, hepatocellular cancer, gastric or stomach cancer including gastrointestinal cancer and gastrointestinal stromal cancer, pancreatic cancer, glioblastoma, brain cancer, nervous system cancer, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, gallbladder cancer, vulval cancer, testicular cancer, thyroid cancer, Kaposi sarcoma, hepatic carcinoma, anal carcinoma, penile carcinoma, non-melanoma skin cancer, melanoma, skin melanoma, superficial spreading melanoma, lentigo maligna melanoma, acral lentiginous melanomas, nodular melanomas, multiple myeloma and B-cell lymphoma (including Hodgkin lymphoma; non-Hodgkin lymphoma, such as e.g., low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukaemia (CLL); acute lymphoblastic leukaemia (ALL); hairy cell leukaemia; chronic myeloblastic leukaemia (CML); Acute Myeloblastic Leukaemia (AML); and post-transplant lymphoproliferative disorder (PTLD), as well as abnormal vascular proliferation associated with phakomatoses, oedema (such as that associated with brain tumors), Meigs' syndrome, brain, as well as head and neck cancer, including lip et oral cavity cancer, and associated metastases.

In a preferred embodiment, said cancer is lung cancer, lip et oral cavity cancer, oropharyngeal cancer, nasopharyngeal cancer, laryngeal cancer, prostate cancer, oesophageal cancer, gallbladder cancer, liver cancer, hepatocellular cancer, gastric or stomach cancer including gastrointestinal cancer and gastrointestinal stromal cancer, pancreatic cancer, Hodgkin lymphoma, Non-Hodgkin lymphoma, leukemia, multiple myeloma, Kaposi sarcoma, kidney cancer, bladder cancer, colon cancer, rectal cancer, colorectal cancer, hepatoma, hepatic carcinoma, anal carcinoma, thyroid cancer, non-melanoma skin cancer, skin melanoma, brain cancer, nervous system cancer, testicular cancer, cervical cancer, uterine cancer, endometrial cancer, ovarian cancer, or breast cancer.

In a more preferred embodiment, said cancer is oesophageal cancer, liver cancer, hepatocellular cancer, gastric or stomach cancer including gastrointestinal cancer and gastrointestinal stromal cancer, pancreatic cancer, Hodgkin lymphoma, colon cancer, rectal cancer, colorectal cancer, hepatoma, hepatic carcinoma, anal carcinoma, non-melanoma skin cancer, skin melanoma, cervical cancer, uterine cancer, endometrial cancer, ovarian cancer, or breast cancer.

Preferably, the risk that said subject will develop a cancer is determined in step b) by comparing the level of step a) with a reference level.

The term "reference level", as used herein, refers to the expression level of the cancer marker under consideration, i.e. progastrin, in a reference sample. A "reference sample", as used herein, means a sample obtained from subjects, preferably two or more subjects, known to be free of the disease or, alternatively, from the general population. The suitable reference expression levels of the cancer marker can be determined by measuring the expression levels of said cancer marker in several suitable subjects, and such reference levels can be adjusted to specific subject populations. The reference value or reference level can be an absolute value; a relative value; a value that has an upper or a lower limit; a range of values; an average value; a median value, a mean value, or a value as compared to a particular control or baseline value. A reference value can be based on an individual sample value such as, for example, a value obtained from a sample from the subject being tested, but at an earlier point in time. The reference value can be based on a large number of samples, such as from population of subjects of the chronological age matched group, or based on a pool of samples including or excluding the sample to be tested.

Advantageously, a "reference level" is a predetermined progastrin level, obtained from a biological sample from a subject with a known particular status as regards cancer. In particular embodiments, the reference level used for comparison with the test sample in step (b) may have been obtained from a biological sample from a healthy subject, or from a biological sample from a subject suffering from cancer; it is understood that the reference expression profile can also be obtained from a pool of biological samples of healthy subjects or from a pool of samples from subjects having cancer. The present inventors have shown that the level of progastrin in fasting, healthy subjects is 0 pM. In a preferred embodiment, the reference level is 0 pM.

The levels of progastrin can be measured by any method known to the person of skill in the art.

Preferably, determining the levels of progastrin in a sample includes contacting said sample with a progastrin-binding molecule and measuring the binding of said progastrin-binding molecule to progastrin.

When expression levels are measured at the protein level, it may be notably performed using specific progastrin-binding molecules, such as e.g., antibodies, in particular using well known technologies such as cell membrane staining using biotinylation or other equivalent techniques followed by immunoprecipitation with specific antibodies, western blot, ELISA or ELISPOT, enzyme-linked immunosorbant assays (ELISA), radioimmunoassays (RIA), immunohistochemistry (IHC), immunofluorescence (IF), antibodies microarrays, or tissue microarrays coupled to immunohistochemistry. Other suitable techniques include FRET or BRET, single cell microscopic or histochemistry methods using single or multiple excitation wavelength and applying any of the adapted optical methods, such as electrochemical methods (voltametry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, flow cytometry, radioisotopic, magnetic resonance imaging, analysis by polyacrylamide gel electrophoresis (SDS-PAGE); HPLC-Mass Spectroscopy; Liquid Chromatography/Mass Spectrometry/Mass Spectrometry (LC-MS/MS)). All these techniques are well known in the art and need not be further detailed here. These different techniques can be used to measure the progastrin levels.

The progastrin-binding molecules of the present invention, especially the anti-progastrin antibodies, are particularly useful in an immunoassay. The immunoassay may be an enzyme-linked immunosorbent assay (ELISA), a radio-immunoassay (RIA), an immunodiffusion assay, or an immuno-detection assay, such as a surface plasmon resistance assay (e.g. a Biacore® assay), an ELISPOT, slot-blot, or a western blot. As a general guide to such techniques, see for instance, Ausubel et al. (eds) (1987) in "Current Protocols in Molecular Biology" John Wiley and Sons, New York, N.Y.

Antibodies are key reagents in numerous assay techniques used in medical, veterinary and other immunodetection fields. Such tests include many routinely used immunoassay techniques, such as for example, enzyme-linked ELISA, RIA, IHC, and IF assays. The level of progastrin is preferentially assayed by any method known to one of skill in the art using antibodies directed against said protein. Preferably, the level of progastrin is determined using an immunoenzymatic assay, preferably based on techniques chosen between RIA and ELISA, with at least one progastrin-binding molecule. Most preferably, said level is determined by ELISA with at least one progastrin-binding molecule. More preferably, the level of progastrin is measured with one progastrin-binding molecule, using an immunoenzymatic assay, most preferably an ELISA assay.

In a particularly useful embodiment, the method for evaluating the risk of the occurrence of a cancer according to the invention comprises determining the level of progastrin in a biological sample from a subject using an immunoenzymatic assay, preferably based on techniques chosen between RIA and ELISA, with a progastrin-binding molecule.

These techniques are particularly useful, in that they allow the skilled person to assay the presence of progastrin by a simple, reproducible and reliable test. The method of the prior art relied on a semi-quantitative test, i.e., IHC staining of epithelial cells in the whole polyp. Such a method is somewhat unreliable. In particular, because of the degree of subjectivity associated with the assay, it is difficult to compare results obtained by different pathologists. In contrast, the method of the invention is fully quantitative, objective and highly sensitive.

In another particularly useful embodiment, the method according to the invention comprises determining the level of progastrin in a biological sample from a subject using an immunoenzymatic assay, preferably based on techniques chosen between RIA and ELISA, with a progastrin-binding molecule.

Thus the level of progastrin is determined in step a) of the present method by determining the amount of progastrin which is bound by a progastrin-binding molecule, preferably by an antibody recognising progastrin.

By "progastrin-binding molecule", it is herein referred to any molecule that binds progastrin, but does not bind gastrin-17 (G17), gastrin-34 (G34), glycine-extended gastrin-17 (G17-Gly), or glycine-extended gastrin-34 (G34-Gly). The progastrin-binding molecule of the present invention may be any progastrin-binding molecule, such as, for instance, an antibody molecule or a receptor molecule. Preferably, the progastrin-binding molecule is an anti-progastrin antibody or an antigen-binding fragment thereof.

By "binding", "binds", or the like, it is herein meant that the antibody, or antigen-binding fragment thereof, forms a complex with an antigen which, under physiologic conditions, is relatively stable. Methods for determining whether two molecules bind one another are well known in the art and include, for example, equilibrium dialysis, surface plasmon resonance, and the like. In a particular embodiment, said antibody, or antigen-binding fragment thereof, binds to progastrin with an affinity that is at least two-fold greater than its affinity for binding to a non specific molecule such as BSA or casein. In a more particular embodiment, said antibody, or antigen-binding fragment thereof, binds only to progastrin.

In a particular embodiment, a biological sample from the subject is contacted with at least one molecule binding to progastrin, wherein the affinity of said agent for progastrin is of at least 100 nM, at least 90 nM, at least 80 nM, at least 70 nM, at least 60 nM, at least 50 nM, at least 40 nM, at least 30 nM, at least 20 nM, at least 10 nM, at least 5 nM, at least 1 nM, at least 100 pM, at least 10 pM, or at least 1 pM, as determined by a method such as above-described.

In a particular embodiment, the present invention relates to a method for evaluating the risk of the occurrence of a cancer in a subject who has not been previously diagnosed with cancer, comprising the detection of the concentration of progastrin in a biological sample from a subject who has not been diagnosed with cancer, wherein said biological sample is contacted with an anti-hPG antibody, or an antigen-binding fragment thereof.

In a particular embodiment, the present invention relates to a method for the prognosis of cancer, comprising the detection of the concentration of progastrin in a biological sample from a subject who has not been diagnosed with cancer, wherein said biological sample is contacted with an anti-hPG antibody, or an antigen-binding fragment thereof.

The term "antibody" as used herein is intended to include polyclonal and monoclonal antibodies. An antibody (or "immunoglobulin") consists of a glycoprotein comprising at least two heavy (H) chains and two light (L) chains interconnected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (C1q) of the classical complement system. Antibodies can be of different isotypes (namely IgA, IgD, IgE, IgG or IgM).

In a more particular embodiment, said biological sample is contacted with a progastrin-binding antibody, or an antigen-binding fragment thereof, selected from the group consisting of: polyclonal antibodies, monoclonal antibodies, chimeric antibodies, humanized antibodies, single chain antibodies, camelized antibodies, IgA1 antibodies, IgA2 antibodies, IgD antibodies, IgE antibodies, IgG1 antibodies, IgG2 antibodies, IgG3 antibodies, IgG4 antibodies and IgM antibodies.

In addition, a person skilled in the art of generating antibodies will easily select and implement a method for generating polyclonal and/or monoclonal antibodies against a given antigen. Also, a person skilled in the art knows a method to determine the CDRs within light and heavy chains of an antibody.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

The term "monoclonal antibody" designates an antibody arising from a nearly homogeneous antibody population, wherein population comprises identical antibodies except for a few possible naturally-occurring mutations which can be found in minimal proportions. A monoclonal antibody arises from the growth of a single cell clone, such as a hybridoma, and is characterized by heavy chains of one class and subclass, and light chains of one type. Anti-human progastrin (anti-hPG) monoclonal antibodies and their use for diagnosis or therapy are already known in the art, see e.g., WO 2011/083 088 for colorectal cancer, WO 2011/083 090 for breast cancer, WO 2011/083 091 for pancreatic cancer, WO 2011/116 954 for colorectal and gastrointestinal cancer, and WO 2012/013 609 and WO 2011/083089 for liver pathologies.

By the expression "antigen-binding fragment" of an antibody, it is intended to indicate any peptide, polypeptide, or protein retaining the ability to bind to the target (also generally referred to as antigen) of the said antibody, generally the same epitope, and comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, or at least 200 contiguous amino acid residues, of the amino acid sequence of the antibody.

In a particular embodiment, the said antigen-binding fragment comprises at least one CDR of the antibody from which it is derived. Still in a preferred embodiment, the said antigen binding fragment comprises 2, 3, 4 or 5 CDRs, more preferably the 6 CDRs of the antibody from which it is derived.

The "antigen-binding fragments" can be selected, without limitation, in the group consisting of Fv, scFv (sc for single chain), Fab, F(ab')$_2$, Fab', scFv-Fc fragments or diabodies, or fusion proteins with disordered peptides such as XTEN (extended recombinant polypeptide) or PAS motifs, or any fragment of which the half-life time would be increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen-binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target.

In another particular embodiment, a biological sample from a subject is contacted with least one antibody binding to progastrin, wherein said antibody has been obtained by an immunization method known by a person skilled in the art, wherein using as an immunogen a peptide which amino acid sequence comprises the totality or a part of the amino-acid sequence of progastrin. Said antibody may be either polyclonal or monoclonal. When more than one antibodies are used (e.g., 2), the method of the invention can be carried out with either only antibodies of the same type (e.g., two monoclonal antibodies) or antibodies belonging to different types (e.g., one monoclonal ad one polyclonal).

In another particular embodiment, said biological sample is contacted with one such antibody. More particularly, said immunogen comprises a peptide chosen among:

a peptide which amino acid sequence comprises, or consists of, the amino acid sequence of full length progastrin, and particularly full length human progastrin of SEQ ID N° 1, a peptide which amino acid sequence corresponds to a part of the amino acid sequence of progastrin, and particularly full length human progastrin of SEQ ID N° 1, a peptide which amino acid sequence corresponds to a part or to the whole amino acid sequence of the N-terminal part of progastrin, and in particular peptides comprising, or consisting of, the amino acid sequence: SWKPRSQQPDAPLG (SEQ ID N° 2), and a peptide which amino acid sequence corresponds to a part or to the whole amino acid sequence of the C-terminal part of progastrin, and in particular peptides comprising, or consisting of, the amino acid sequence: QGPWLEEEEEAYGWMDFGRRSAEDEN (SEQ ID N° 3), a peptide which amino acid sequence corresponds to a part of the amino acid sequence of the C-terminal part of progastrin, and in particular peptides comprising the amino acid sequence FGRRSAEDEN (SEQ ID N° 40) corresponding to amino acids 71-80 of progastrin The skilled person will easily realize that such immunization may be used to generate either polyclonal or monoclonal antibodies, as desired. Methods for obtaining each of these types of antibodies are well known in the art.

Examples of monoclonal antibodies which were generated by using an immunogen comprising the amino-acid sequence "SWKPRSQQPDAPLG" (SEQ ID N° 2), corresponding to the amino acid sequence 1-14 of human progastrin (N-terminal extremity) include, but are not restricted to, monoclonal antibodies designated as: mAb3, mAb4, mAb16, and mAb19 and mAb20, as described in the following Table 1 to Table 4. Other monoclonal antibodies have been described, although it is not clear whether these antibodies actually bind progastrin (WO 2006/032980). Experimental results of epitope mapping show that mAb3, mAb4, mAb16, and mAb19 and mAb20 do specifically bind an epitope within said hPG N-terminal amino acid sequence. Polyclonal antibodies recognizing specifically an epitope within the N-terminus of progastrin represented by SEQ ID NO. 2, have been described in the art (see e.g. WO 2011/083088).

TABLE 1

| Hybridoma deposit | mAb | Amino acid sequences | | SEQ ID No |
|---|---|---|---|---|
| 6B5B11C10 | mAb3 | VH CDR 1 | GYIFTSYW | SEQ ID No 4 |
| | | VH CDR 2 | FYPGNSDS | SEQ ID No 5 |
| | | VH CDR 3 | TRRDSPQY | SEQ ID No 6 |
| | | VL CDR 1 | QSIVHSNGNTY | SEQ ID No 7 |
| | | VL CDR 2 | KVS | SEQ ID No 8 |
| | | VL CDR 3 | FQGSHVPFT | SEQ ID No 9 |

TABLE 2

| Hybridoma deposit | mAb | Amino acid sequences | | SEQ ID No |
|---|---|---|---|---|
| 20D2C3G2 | mAb4 | VH CDR 1 | GYTFSSW | SEQ ID No 10 |
| | | VH CDR 2 | FLPGSGST | SEQ ID No 11 |
| | | VH CDR 3 | ATDGNYDWFAY | SEQ ID No 12 |
| | | VL CDR 1 | QSLVHSSGVTY | SEQ ID No 13 |
| | | VL CDR 2 | KVS | SEQ ID No 14 |
| | | VL CDR 3 | SQSTHVPPT | SEQ ID No 15 |

TABLE 3

| Hybridoma deposit | mAb | Amino acid sequences | | SEQ ID No |
|---|---|---|---|---|
| 1E9D9B6 | mAb16 | VH CDR 1 | GYTFTSYY | SEQ ID No 16 |
| | | VH CDR 2 | INPSNGGT | SEQ ID No 17 |
| | | VH CDR 3 | TRGGYYPFDY | SEQ ID No 18 |
| | | VL CDR 1 | QSLLDSDGKTY | SEQ ID No 19 |
| | | VL CDR 2 | LVS | SEQ ID No 20 |
| | | VL CDR 3 | WQGTHSPYT | SEQ ID No 21 |

TABLE 4

| Hybridoma deposit | mAb | Amino acid sequences | | SEQ ID No |
|---|---|---|---|---|
| 1B3B4F11 | mAb19 | VH CDR 1 | GYSITSDYA | SEQ ID No 22 |
| | | VH CDR 2 | ISFSGYT | SEQ ID No 23 |
| | | VH CDR 3 | AREVNYGDSYHFDY | SEQ ID No 24 |
| | | VL CDR 1 | SQHRTYT | SEQ ID No 25 |
| | | VL CDR 2 | VKKDGSH | SEQ ID No 26 |
| | | VL CDR 3 | GVGDAIKGQSVFV | SEQ ID No 27 |

Examples of monoclonal antibodies that can be generated by using an immunogen comprising the amino-acid sequence "QGPWLEEEEEAYGWMDFGRRSAEDEN" (SEQ ID N° 3), (C-terminal part of progastrin) corresponding to the amino acid sequence 55-80 of human progastrin include, but are not restricted to antibodies designated as: mAb8 and mAb13 in the following Table 5 and 6. Experimental results of epitope mapping show that mAb13 do specifically bind an epitope within said hPG C-terminal amino acid sequence.

TABLE 5

| Hybridoma deposit | mAb | Amino acid sequences | | SEQ ID No |
|---|---|---|---|---|
| 1C10D3B9 | mAb8 | VH CDR 1 | GFTFTTYA | SEQ ID No 28 |
| | | VH CDR 2 | ISSGGTYT | SEQ ID No 29 |
| | | VH CDR 3 | ATQGNYSLDF | SEQ ID No 30 |
| | | VL CDR 1 | KSLRHTKGITF | SEQ ID No 31 |
| | | VL CDR 2 | QMS | SEQ ID No 32 |
| | | VL CDR 3 | AQNLELPLT | SEQ ID No 33 |

TABLE 6

| Hybridoma deposit | mAb | Amino acid sequences | | SEQ ID No |
|---|---|---|---|---|
| 2C6C3C7 | mAb13 | VH CDR 1 | GFIFSSYG | SEQ ID No 34 |
| | | VH CDR 2 | INTFGDRT | SEQ ID No 35 |
| | | VH CDR 3 | ARGTGTY | SEQ ID No 36 |
| | | VL CDR 1 | QSLLDSDGKTY | SEQ ID No 37 |
| | | VL CDR 2 | LVS | SEQ ID No 38 |
| | | VL CDR 3 | WQGTHFPQT | SEQ ID No 39 |

Other examples include anti-hPG monoclonal and/or polyclonal antibodies generated by using an immunogen comprising an amino acid sequence of SEQ ID N° 40.

In a more particular embodiment, in a method according to the invention said biological sample is contacted with at least one anti-hPG antibody or antigen-binding fragment thereof, preferably with one anti-hPG antibody or antigen-binding fragment thereof, wherein said anti-hPG antibody is chosen among N-terminal anti-hPG antibodies and C-terminal anti-hPG antibodies.

The terms "N-terminal anti-hPG antibodies" and "C-terminal anti-hPG antibodies" designate antibodies binding to an epitope comprising amino acids located in the N-terminal part of hPG or to an epitope comprising amino acids located in the C-terminal part of hPG, respectively. Preferably, the term "N-terminal anti-hPG antibodies" refers to antibodies binding to an epitope located in a domain of progastrin whose sequence is represented by SEQ ID NO. 2. In another preferred embodiment, the term "C-terminal anti-hPG antibodies" refers to antibodies binding to an epitope located in a domain of progastrin whose sequence is represented by SEQ ID NO. 3.

The term "epitope" is a region of an antigen that is bound by an antibody. Epitopes may be defined as structural or functional. Functional epitopes are generally a subset of the structural epitopes and have those amino acids that directly contribute to the affinity of the interaction. Epitopes may also be conformational. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. The determination of the epitope bound by an antibody may be performed by any epitope mapping technique, known by a person skilled in the art. An epitope may comprise different amino acids which located sequentially within the amino acid sequence of a protein. An epitope may also comprise amino acids which are not located sequentially within the amino acid sequence of a protein.

In a particular embodiment of the method of the invention, said antibody is a monoclonal antibody chosen in the group consisting of:

- A monoclonal antibody comprising a heavy chain comprising at least one, preferentially at least two, preferentially three, of CDR-H1, CDR-H2 and CDR-H3 of amino acid sequences SEQ ID N° 4, 5 and 6, respectively, or sequences with at least 80%, preferably 85%, 90%, 95% and 98% identity after optimal alignment with sequences SEQ ID N° 4, 5 and 6, respectively, and a light chain comprising at least one, preferentially at least two, preferentially three, of CDR-L1, CDR-L2 and CDR-L3 of amino acid sequences SEQ ID N° 7, 8 and 9, respectively, or sequences with at least 80%, preferably 85%, 90%, 95% and 98% identity after optimal alignment with sequences SEQ ID N° 7, 8 and 9, respectively,
- A monoclonal antibody comprising a heavy chain comprising at least one, preferentially at least two, preferentially three, of CDR-H1, CDR-H2 and CDR-H3 of amino acid sequences SEQ ID N° 10, 11 and 12, respectively, or sequences with at least 80%, preferably 85%, 90%, 95% and 98% identity after optimal alignment with sequences SEQ ID N° 10, 11 and 12, respectively, and a light chain comprising at least one, preferentially at least two, preferentially three, of CDR-L1, CDR-L2 and CDR-L3 of amino acid sequences SEQ ID N° 13, 14 and 15, respectively, or sequences with at least 80%, preferably 85%, 90%, 95% and 98% identity after optimal alignment with sequences SEQ ID N° 13, 14 and 15, respectively,
- A monoclonal antibody comprising a heavy chain comprising at least one, preferentially at least two, preferentially three, of CDR-H1, CDR-H2 and CDR-H3 of amino acid sequences SEQ ID N° 16, 17 and 18, respectively, or sequences with at least 80%, preferably 85%, 90%, 95% and 98% identity after optimal alignment with sequences SEQ ID N° 16, 17 and 18, respectively, and a light chain comprising at least one, preferentially at least two, preferentially three, of CDR-L1, CDR-L2 and CDR-L3 of amino acid sequences SEQ ID N° 19, 20 and 21, respectively, or sequences with at least 80%, preferably 85%, 90%, 95% and 98% identity after optimal alignment with sequences SEQ ID N° 19, 20 and 21, respectively,
- A monoclonal antibody comprising a heavy chain comprising at least one, preferentially at least two, preferentially three, of CDR-H1, CDR-H2 and CDR-H3 of amino acid sequences SEQ ID N° 22, 23 and 24, respectively, or sequences with at least 80%, preferably 85%, 90%, 95% and 98% identity after optimal alignment with sequences SEQ ID N° 22, 23 and 24, respectively, and a light chain comprising at least one, preferentially at least two, preferentially three, of CDR-L1, CDR-L2 and CDR-L3 of amino acid sequences SEQ ID N° 25, 26 and 27, respectively, or sequences with at least 80%, preferably 85%, 90%, 95% and 98% identity after optimal alignment with sequences SEQ ID N° 25, 26 and 27, respectively,
- A monoclonal antibody comprising a heavy chain comprising at least one, preferentially at least two, preferentially at least three, of CDR-H1, CDR-H2 and CDR-H3 of amino acid sequences SEQ ID N° 28, 29 and 30, respectively, or sequences with at least 80%, preferably 85%, 90%, 95% and 98% identity after optimal alignment with sequences SEQ ID N° 28, 29 and 30, respectively, and a light chain comprising at least one, preferentially at least two, preferentially three, of CDR-L1, CDR-L2 and CDR-L3 of amino acid sequences SEQ ID N° 31, 32 and 33, respectively, or sequences with at least 80%, preferably 85%, 90%, 95% and 98% identity after optimal alignment with sequences SEQ ID N° 31, 32 and 33, respectively
- A monoclonal antibody comprising a heavy chain comprising at least one, preferentially at least two, preferentially three, of CDR-H1, CDR-H2 and CDR-H3 of amino acid sequences SEQ ID N° 34, 35 and 36, respectively, or sequences with at least 80%, preferably 85%, 90%, 95% and 98% identity after optimal alignment with sequences SEQ ID N° 34, 35 and 36, respectively, and a light chain comprising at least one, preferentially at least two, preferentially three, of CDR-L1, CDR-L2 and CDR-L3 of amino acid sequences SEQ ID N° 37, 38 and 39, respectively, or sequences with at least 80%, preferably 85%, 90%, 95% and 98% identity after optimal alignment with sequences SEQ ID N° 37, 38 and 39, respectively, and
- A monoclonal antibody produced by the hybridoma deposited at the CNCM, Institut Pasteur, 25-28 rue du Docteur Roux, 75724 Paris CEDEX 15, France, on 27 Dec. 2016, under reference I-5158.

As used herein, the "percentage identity" or "% identity" between two sequences of nucleic acids or amino acids refers to the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of methods known by a man skilled in the art.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

In another particular embodiment, the antibody used in the method of the invention is a humanised antibody.

As used herein, "humanised antibody" refers to an antibody that contains CDR regions derived from an antibody of nonhuman origin, the other parts of the antibody molecule being derived from one or several human antibodies. In addition, some of the skeleton segment residues (called FR for framework) can be modified if necessary to preserve binding affinity, by using techniques well known to the person of skill in the art (Jones et al., Nature, 321:522-525, 1986). The goal of humanisation is a reduction in the immunogenicity of a xenogenic antibody, such as a murine antibody, for introduction into a human, while maintaining the full antigen binding affinity and specificity of the antibody.

Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(4/5): 489-498; Studnicka G. M. et al., 1994, Protein Engineering 7(6): 805-814; Roguska M. A. et al., 1994, Proc. Natl. Acad. ScL U.S.A., 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741.

In a more particular embodiment, the antibody used in the method of the invention is a humanised antibody chosen in the group consisting of:

A humanised antibody comprising a heavy chain comprising at least one, preferentially at least two, preferentially three, of CDR-H1, CDR-H2 and CDR-H3 of amino acid sequences SEQ ID N° 4, 5 and 6, respectively, or sequences with at least 80%, preferably 85%, 90%, 95% and 98% identity after optimal alignment with sequences SEQ ID N° 4, 5 and 6, respectively, and a light chain comprising at least one, preferentially at least two, preferentially three, of CDR-L1, CDR-L2 and CDR-L3 of amino acid sequences SEQ ID N° 7, 8 and 9, respectively, or sequences with at least 80%, preferably 85%, 90%, 95% and 98% identity after optimal alignment with sequences SEQ ID N° 7, 8 and 9, respectively, A humanised antibody comprising a heavy chain comprising at least one, preferentially at least two, preferentially three, of CDR-H1, CDR-H2 and CDR-H3 of amino acid sequences SEQ ID N° 10, 11 and 12, respectively, or sequences with at least 80%, preferably 85%, 90%, 95% and 98% identity after optimal alignment with sequences SEQ ID N° 10, 11 and 12, respectively, and a light chain comprising at least one, preferentially at least two, preferentially three, of CDR-L1, CDR-L2 and CDR-L3 of amino acid sequences SEQ ID N° 13, 14 and 15, respectively, or sequences with at least 80%, preferably 85%, 90%, 95% and 98% identity after optimal alignment with sequences SEQ ID N° 13, 14 and 15, respectively, A humanised antibody comprising a heavy chain comprising at least one, preferentially at least two, preferentially three, of CDR-H1, CDR-H2 and CDR-H3 of amino acid sequences SEQ ID N° 16, 17 and 18, respectively, or sequences with at least 80%, preferably 85%, 90%, 95% and 98% identity after optimal alignment with sequences SEQ ID N° 16, 17 and 18, respectively, and a light chain comprising at least one, preferentially at least two, preferentially three, of CDR-L1, CDR-L2 and CDR-L3 of amino acid sequences SEQ ID N° 19, 20 and 21, respectively, or sequences with at least 80%, preferably 85%, 90%, 95% and 98% identity after optimal alignment with sequences SEQ ID N° 19, 20 and 21, respectively, A humanised antibody comprising a heavy chain comprising at least one, preferentially at least two, preferentially three, of CDR-H1, CDR-H2 and CDR-H3 of amino acid sequences SEQ ID N° 22, 23 and 24, respectively, or sequences with at least 80%, preferably 85%, 90%, 95% and 98% identity after optimal alignment with sequences SEQ ID N° 22, 23 and 24, respectively, and a light chain comprising at least one, preferentially at least two, preferentially three, of CDR-L1, CDR-L2 and CDR-L3 of amino acid sequences SEQ ID N° 25, 26 and 27, respectively, or sequences with at least 80%, preferably 85%, 90%, 95% and 98% identity after optimal alignment with sequences SEQ ID N° 25, 26 and 27, respectively, A humanised antibody comprising a heavy chain comprising at least one, preferentially at least two, preferentially three, of CDR-H1, CDR-H2 and CDR-H3 of amino acid sequences SEQ ID N° 28, 29 and 30, respectively, or sequences with at least 80%, preferably 85%, 90%, 95% and 98% identity after optimal alignment with sequences SEQ ID N° 28, 29 and 30, respectively, and a light chain comprising at least one, preferentially at least two, preferentially three, of CDR-L1, CDR-L2 and CDR-L3 of amino acid sequences SEQ ID N° 31, 32 and 33, respectively, or sequences with at least 80%, preferably 85%, 90%, 95% and 98% identity after optimal alignment with sequences SEQ ID N° 31, 32 and 33, respectively, and A humanised antibody comprising a heavy chain comprising at least one, preferentially at least two, preferentially three, of CDR-H1, CDR-H2 and CDR-H3 of amino acid sequences SEQ ID N° 34, 35 and 36, respectively, or sequences with at least 80%, preferably 85%, 90%, 95% and 98% identity after optimal alignment with sequences SEQ ID N° 34, 35 and 36, respectively, and a light chain comprising at least one, preferentially at least two, preferentially three, of CDR-L1, CDR-L2 and CDR-L3 of amino acid sequences SEQ ID N° 37, 38 and 39, respectively, or sequences with at least 80%, preferably 85%, 90%, 95% and 98% identity after optimal alignment with sequences SEQ ID N° 37, 38 and 39, respectively, wherein said antibody also comprises constant regions of the light-chain and the heavy-chain derived from a human antibody.

In a first embodiment, a method according to the invention comprises contacting a biological sample with at least one anti-hPG antibody binding to an epitope of hPG, preferably one anti-hPG antibody binding to an epitope of hPG, wherein said epitope is located within the C-terminal part of hPG. Alternatively, the method according to the invention comprises contacting a biological sample with at least one anti-hPG antibody binding to an epitope of hPG, preferably one anti-hPG antibody binding to an epitope of hPG, wherein said epitope is located within the N-terminal part of hPG.

In a more specific embodiment, a method according to the invention comprises contacting a biological sample with at least one anti-hPG antibody binding to an epitope of hPG, preferably one anti-hPG antibody binding to an epitope of hPG, wherein said epitope includes an amino acid sequence corresponding to an amino acid sequence of the N-terminal part of progastrin chosen among an amino acid sequence corresponding to amino acids 10 to 14 of hPG, amino acids 9 to 14 of hPG, amino acids 4 to 10 of hPG, amino acids 2 to 10 of hPG and amino acids 2 to 14 of hPG, wherein the amino acid sequence of hPG is SEQ ID N° 1.

In a more specific embodiment, a method according to the invention comprises contacting a biological sample with at least one anti-hPG antibody binding to an epitope of hPG, preferably one anti-hPG antibody binding to an epitope of hPG, wherein said epitope includes an amino acid sequence corresponding to an amino acid sequence of the C-terminal part of progastrin, chosen among an amino acid sequence corresponding to amino acids 71 to 74 of hPG, amino acids 69 to 73 of hPG, amino acids 71 to 80 of hPG (SEQ ID N° 40), amino acids 76 to 80 of hPG, and amino acids 67 to 74 of hPG, wherein the amino acid sequence of hPG is SEQ ID N° 1.

In a particular embodiment of the method of the invention, said method comprises a step of contacting a biological sample from a subject with a first agent which binds to a first part of progastrin and with a second agent which binds to a second part of progastrin. In a more particular embodiment, wherein said progastrin-binding molecule is an antibody, a biological sample from a subject is contacted with an antibody which binds to a first epitope of progastrin and with a second antibody which binds to a second epitope of progastrin.

According to a preferred embodiment, said first antibody is bound to an insoluble or partly soluble carrier. Binding of progastrin by said first antibody results in capture of progastrin from said biological sample. Preferably, said first antibody is an antibody binding to an epitope of hPG, wherein said epitope includes an amino acid sequence corresponding to an amino acid sequence of the C-terminal part of progastrin, as described above. More preferably, said first antibody is monoclonal antibody Mab14, produced by hybridoma 2H9F4B7, described in WO 2011/083088. Hybridoma 2H9F4B7 was deposited under the Budapest Treaty at the CNCM, Institut Pasteur, 25-28 rue du Docteur Roux, 75724 Paris CEDEX 15, France, on 27 Dec. 2016, under reference I-5158.

According to another preferred embodiment, said second antibody is labelled with a detectable moiety, as described below. Binding of progastrin by second antibody enables the detection of the progastrin molecules which were present in the biological sample. Further, binding of progastrin by second antibody enables the quantification of the progastrin molecules which were present in the biological sample. Preferably, said second antibody is an antibody binding to an epitope of hPG, wherein said epitope includes an amino acid sequence corresponding to an amino acid sequence of the N-terminal part of progastrin, as described above. More preferably, said N-terminal antibody is a polyclonal antibody, as described above. Alternatively, it is also possible to use a monoclonal antibody biding an epitope within the N-terminus of progastrin, such as e.g. the N-terminus monoclonal antibodies described above, notably a monoclonal antibody comprising a heavy chain comprising CDR-H1, CDR-H2 and CDR-H3 of amino acid sequences SEQ ID N° 16, 17 and 18, respectively, and a light chain comprising CDR-L1, CDR-L2 and CDR-L3 of amino acid sequences SEQ ID N° 19, 20 and 21.

In a particularly preferred embodiment, the first antibody is bound to an insoluble or partly soluble carrier and the second antibody is labelled with a detectable moiety.

In a particular embodiment, the method of the present invention comprises the determination of the concentration of progastrin in a biological sample from a human subject who has never been previously diagnosed with cancer.

In another particular embodiment, the method of the present invention comprises the determination of the concentration of progastrin in a biological sample from a human subject who has never been previously diagnosed with cancer, wherein said biological sample is selected from blood, serum and plasma.

In a more particular embodiment, the method of the present invention comprises contacting a plasma sample from said subject with at least one anti-hPG antibody, notably with one anti-hPG antibody, and determining the concentration of progastrin in said sample, wherein a concentration of progastrin superior to 10 pM in said plasma is indicative of a risk of developing cancer in said subject. In other words, a concentration of progastrin superior to 10 pM in said plasma is indicative of a bad prognosis in said subject.

Still more preferably, the method of the present invention comprises contacting a plasma sample from said subject with at least one anti-hPG antibody, notably with one anti-hPG antibody, and determining the concentration of progastrin in said sample, wherein a concentration of progastrin superior to 10 pM, preferably to 20 pM, more preferably to 30 pM, still more preferably to 40 pM, even more preferably to 50 pM in said plasma sample is indicative of a risk of developing cancer in said subject.

In another aspect, the present invention relates to a method of treating a cancer in a patient who had never been diagnosed for cancer, said method comprising the steps of:
 a) evaluating the risk of said patient to develop a cancer by any of the methods described above; and
 b) treating said cancer if there is risk according to a).

The method of the invention is particularly advantageous, because it allows cancers to be identified at a very early stage. It is known in the art that the earlier the identification of the cancer, the higher the chances of remission. In addition, the patient can be treated with anti-cancer drugs which are not too aggressive, thus lessening the chances of side-effects whilst maintaining therapeutic efficiency.

In a particular embodiment, a method according to the invention comprises comparing the concentration of progastrin in a biological sample obtained from a patient with a predetermined value of concentration of progastrin in the sample, in a more particular embodiment, said predetermined value is chosen among: a mean, or average, of sample values based on the mean, or average, determination of the value in a population free of cancer, a progastrin concentration value obtained when the patient was known to be free of cancer.

In yet another aspect, the invention also provides a composition for use in the methods described above. According to this aspect of the invention, the composition is for evaluating the risk of the occurrence of cancer in a subject who has never been diagnosed previously with cancer, wherein said composition comprises at least one progastrin-binding antibody, or an antigen-binding fragment thereof.

In a first embodiment, a composition according to the invention comprises an antibody recognizing an epitope including an amino acid sequence corresponding to an amino acid sequence of progastrin.

In a more specific embodiment, a composition according to the invention comprises an antibody recognizing an epitope of progastrin wherein said epitope includes an amino acid sequence corresponding to an amino acid sequence of the N-terminal part of progastrin, wherein said amino acid sequence may include residues 10 to 14 of hPG, residues 9 to 14 of hPG, residues 4 to 10 of hPG, residues 2 to 10 of hPG or residues 2 to 14 of hPG, wherein the amino acid sequence of hPG is SEQ ID N° 1.

In a more specific embodiment, a composition according to the invention comprises an antibody recognizing an epitope of progastrin wherein said epitope includes an amino acid sequence corresponding to an amino acid sequence of the C-terminal part of progastrin, wherein said amino acid sequence may include residues 71 to 74 of hPG, residues 69 to 73 of hPG, residues 71 to 80 of hPG (SEQ ID N° 40), residues 76 to 80 of hPG, or residues 67 to 74 of hPG, wherein the amino acid sequence of hPG is SEQ ID N° 1.

In still another aspect, the present invention provides a kit useful for the methods described above, said kit comprising any of the antibodies of the invention. Packaged materials comprising a combination of reagents in predetermined amounts with instructions for performing the methods described above, e.g. kits, are also within the scope of the invention. Preferably, said kit comprises at least one antibody of the invention, more preferably two.

For example, in a first embodiment, said kit comprises a first antibody bound to an insoluble or partly soluble carrier. Preferably, said first antibody is an antibody binding to an epitope of hPG, wherein said epitope includes an amino acid sequence corresponding to an amino acid sequence within the C-terminal part of progastrin, as described above. More preferably, said first antibody is monoclonal antibody Mab14, produced by hybridoma 2H9F4B7, described in WO 2011/083088. Hybridoma 2H9F4B7 was deposited under the Budapest Treaty at the CNCM, Institut Pasteur, 25-28 rue du Docteur Roux, 75724 Paris CEDEX 15, France, on 27 Dec. 2016, under reference I-5158. In another embodiment, polyclonal or monoclonal antibodies, or antigen-binding fragment or derivative thereof, as detailed herein are provided labeled with a detectable moiety, such that they may be packaged and used, for example, in kits, to identify cells having the aforementioned antigen, either before secretion or bound to the receptor for progastrin. Non-limiting examples of such labels include fluorophores such as fluorescein isothiocyanate; chromophores, radionuclides, biotin or enzymes. Such labeled antibodies or binding fragments may be used for the histological localization of the antigen, ELISA, cell sorting, as well as other immunological techniques for detecting or quantifying progastrin, and cells bearing this antigen, for example. Preferably, said labeled antibody is an antibody binding to an epitope of hPG, wherein said epitope includes an amino acid sequence corresponding to an amino acid sequence within the N-terminal part of progastrin, as described above. More preferably, said N-terminal antibody is a polyclonal antibody, as described above. Alternatively, it is also possible to use a monoclonal antibody biding an epitope within the N-terminus of progastrin, such as e.g. the N-terminus monoclonal antibodies described above, notably a monoclonal antibody comprising a heavy chain comprising CDR-H1, CDR-H2 and CDR-H3 of amino acid sequences SEQ ID N° 16, 17 and 18, respectively, and a light chain comprising CDR-L1, CDR-L2 and CDR-L3 of amino acid sequences SEQ ID N° 19, 20 and 21.

Thus in a most preferred embodiment, the kit of the invention comprises:
    a first anti-progastrin antibody, wherein said antibody is wherein said first anti-progastrin antibody is a monoclonal antibody produced by the hybridoma deposited at the CNCM, Institut Pasteur, 25-28 rue du Docteur Roux, 75724 Paris CEDEX 15, France, on 27 Dec. 2016, under reference I-5158; and
    a second anti-progastrin antibody, wherein said second anti-progastrin antibody is a polyclonal antibody binding an epitope within the N-terminus of progastrin or a monoclonal antibody comprising a heavy chain comprising the following three CDRs, CDR-H1, CDR-H2 and CDR-H3 of amino acid sequences SEQ ID N° 16, 17 and 18, respectively, and a light chain comprising the following three CDRs, CDR-L1, CDR-L2 and CDR-L3 of amino acid sequences SEQ ID N° 19, 20 and 21, respectively.

The invention includes kits wherein the antibody, or antigen-binding fragment or derivative thereof, is labeled.

The reagents may be provided as dry powders, usually lyophilized, including excipients which on dissolution will provide a reagent solution having the appropriate concentration.

The kit contains the antibodies for detection and quantification of progastrin in vitro, e.g. in an ELISA or a Western blot. The antibody of the present invention can be provided in a kit for detection and quantification of progastrin in vitro, e.g. in an ELISA or a Western blot. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention. The label or package insert may provide a description of the composition as well as instructions for the intended in vitro or diagnostic use.

Kits are also provided for use as a positive control for purification or immunoprecipitation of progastrin from cells. For isolation and purification of progastrin, the kit can contain the antibody described herein, or an antigen-binding fragment or derivative thereof, coupled to beads (e.g., sepharose beads). Kits can be provided which contain the antibodies for detection and quantification of progastrin in vitro or ex vivo, e.g. in an ELISA or a Western blot. The kit comprises a container and a label or package insert on or associated with the container. The container holds a composition comprising at least one antibody, or binding fragment or derivative thereof, of the invention. Additional containers may be included that contain, e.g., diluents and buffers, control antibodies. The label or package insert may provide a description of the composition as well as instructions for the intended in vitro or diagnostic use.

The invention also relates to a product/computer program containing a set of instructions characteristic of the implementation of the inventive method.

The invention also relates to a processing system including a computation unit and an input interface, characterized in that said system includes means for implementing the method for determining the risk of developing cancer as disclosed herein.

Figure 13:
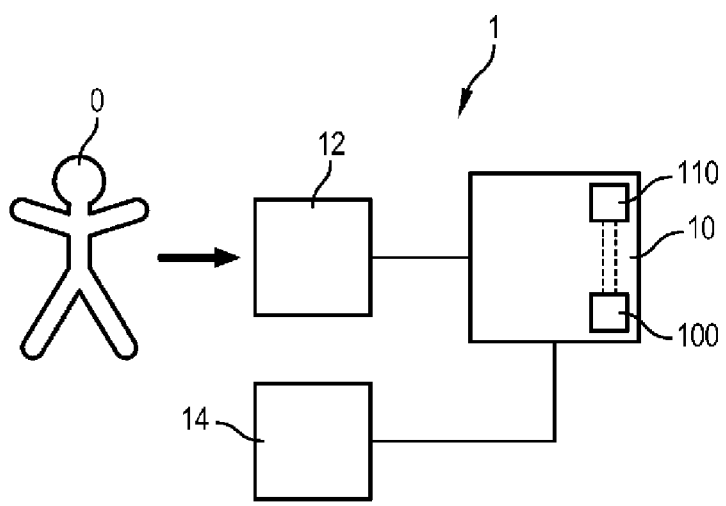

In reference to FIG. 13, a device (1) according to a particular embodiment of the present invention includes a computation unit (10) capable of following computer instructions and processing data. One such computation unit preferentially includes a microprocessor (110), which can be of any type known in the state of the art. The computation unit (10) also has a storage unit (100) that is capable of receiving a computer program including a set of instructions characteristic of the implementation of the method, and is capable of storing data.

The device (1) also includes an input interface (12) connected to the computation unit (10) enabling an operator (O) of the device (1) to enter data to be treated. One such input interface (12) includes any element enabling the entry of such data destined for the computation unit (10) such as a keyboard element optionally associated with a pointing device element.

Preferentially, the computation unit further includes an output interface (14) such as a screen that on the one hand enables the user to verify the integrity of the data entered but on the other hand enables the computation unit (10) to be able to interact with the operator (O).

The device (1) can be integrated in a single system such as a computer, a smartphone or any other system known in the state of the art enabling implementation of the inventive method. The operator (O) can be of any skill level and thus may or may not have medical qualifications.

It is notably envisaged according to a particular embodiment of the present invention that the data entered by the operator (O) are sent via a network (the Internet, for example) preferentially in a secure manner to a remote server comprising a computation unit capable of implementing the inventive method and thus of treating the data received by the server. Optionally, after said processing, the server returns the result of the analysis to the user via the same network or another. Optionally, the server records the data and/or the result of the analysis on a means of recording. Obviously, means of guaranteeing the anonymity of the physiological/clinical characteristics of the donor and the recipient can be envisaged.

Thus, one such device (1) enables implementation of the inventive method, i.e., it enables implementation of the following steps:
- entering physiological/clinical characteristics using the input interface (12) into a computation unit (10) (step 22), said characteristics including the level of progastrin in the sample (10) (step 23),
- optionally normalizing said progastrin level via data processing by the computation unit (10) (step 24), and
- analyzing said risk score so as to determine risk of development of cancer (step 25).

Thus, the method of the invention can be implemented not only by clinical or hospital personnel but also by all persons involved in clinical research (pharmaceutical industry, scientists, doctors, etc.) or even by the general public.

The examples that follow are merely exemplary of the scope of this invention and content of this disclosure. One skilled in the art can devise and construct numerous modifications to the examples listed below without departing from the scope of this invention.

FIGURE LEGENDS

FIG. 1: Receiver operating characteristic (ROC) curve for colorectal cancer (upper panel) with the area under the ROC curve and the statistical analysis (lower panel).

Figure 2:
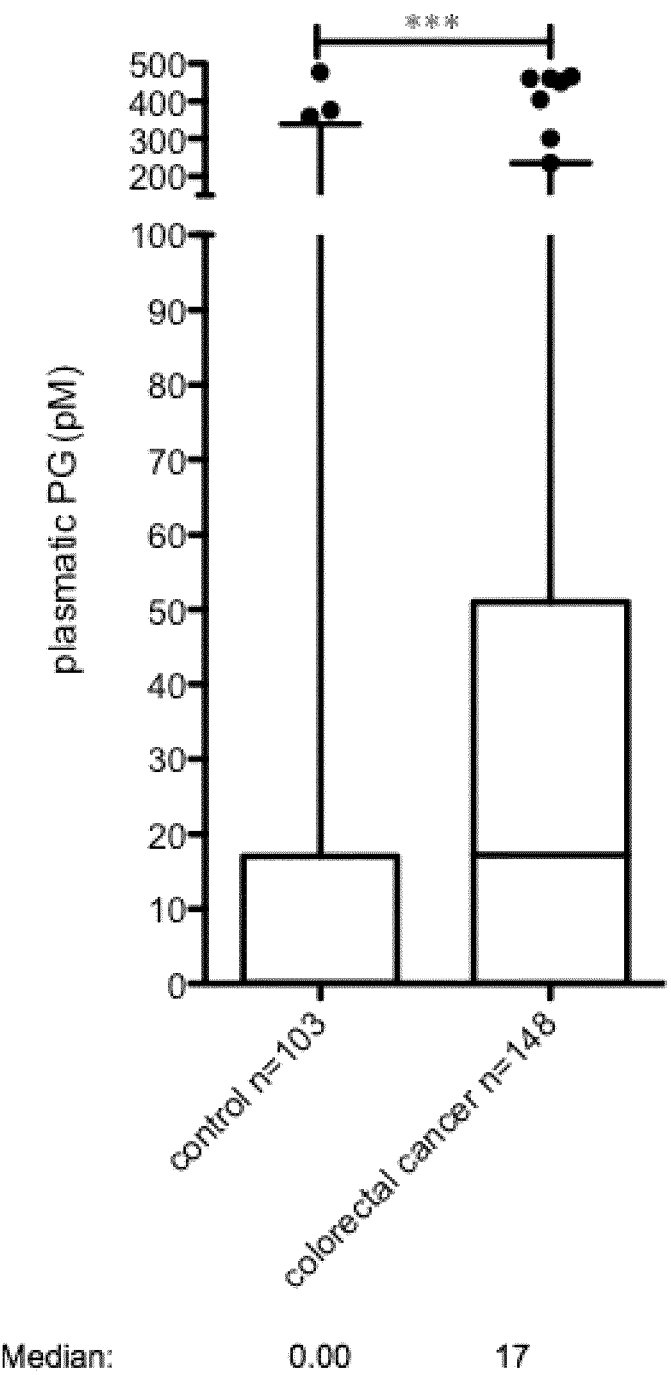

FIG. 2: median plasmatic concentration of progastrin in colorectal cancer patients (n=148), and in control patients (n=103) using a combination of an N-terminus polyclonal antibody and a C-terminus polyclonal antibody—Mann Whitney test two-tailed, ***p<0.0001.

Figure 3:
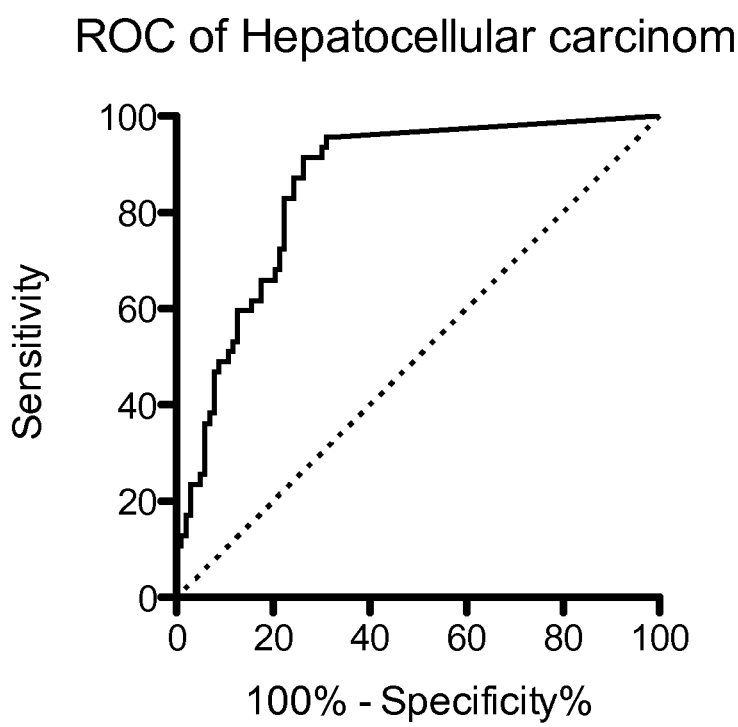

FIG. 3: Receiver operating characteristic (ROC) curve for hepatocellular carcinoma (upper panel) with the area under the ROC curve and the statistical analysis (lower panel).

Figure 4:
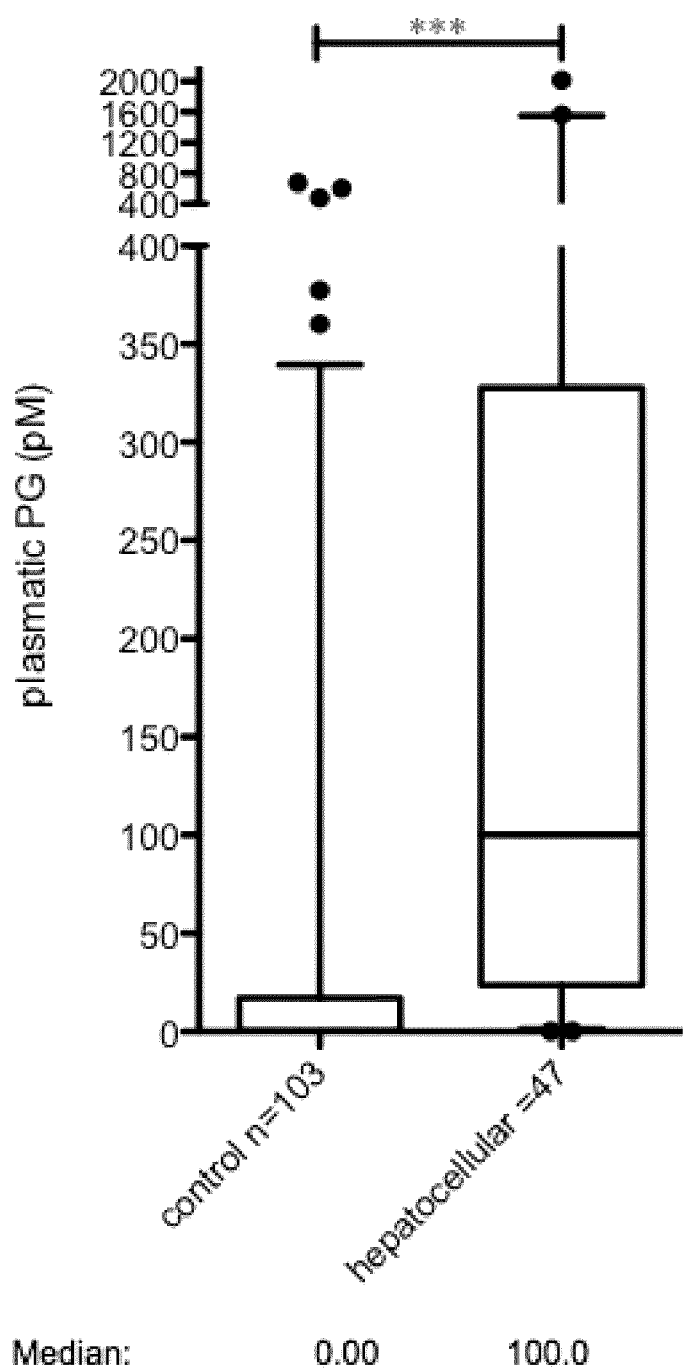

FIG. 4: median plasmatic concentration of progastrin in hepatocellular carcinoma patients (n=47), and in control patients (n=103) using a combination of an N-terminus polyclonal antibody and a C-terminus polyclonal antibody—Mann Whitney test two-tailed, ***p<0.0001

Figure 5:
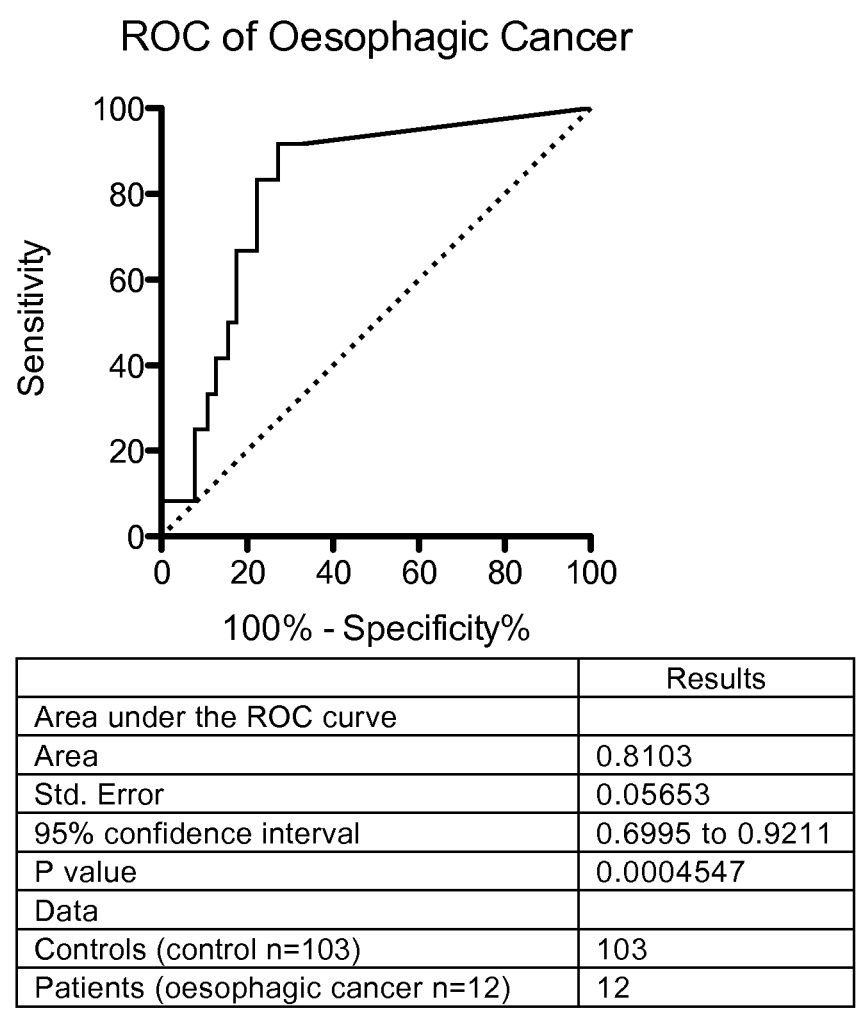

FIG. 5: Receiver operating characteristic (ROC) curve for oesophagic cancer (upper panel) with the area under the ROC curve and the statistical analysis (lower panel).

Figure 6:
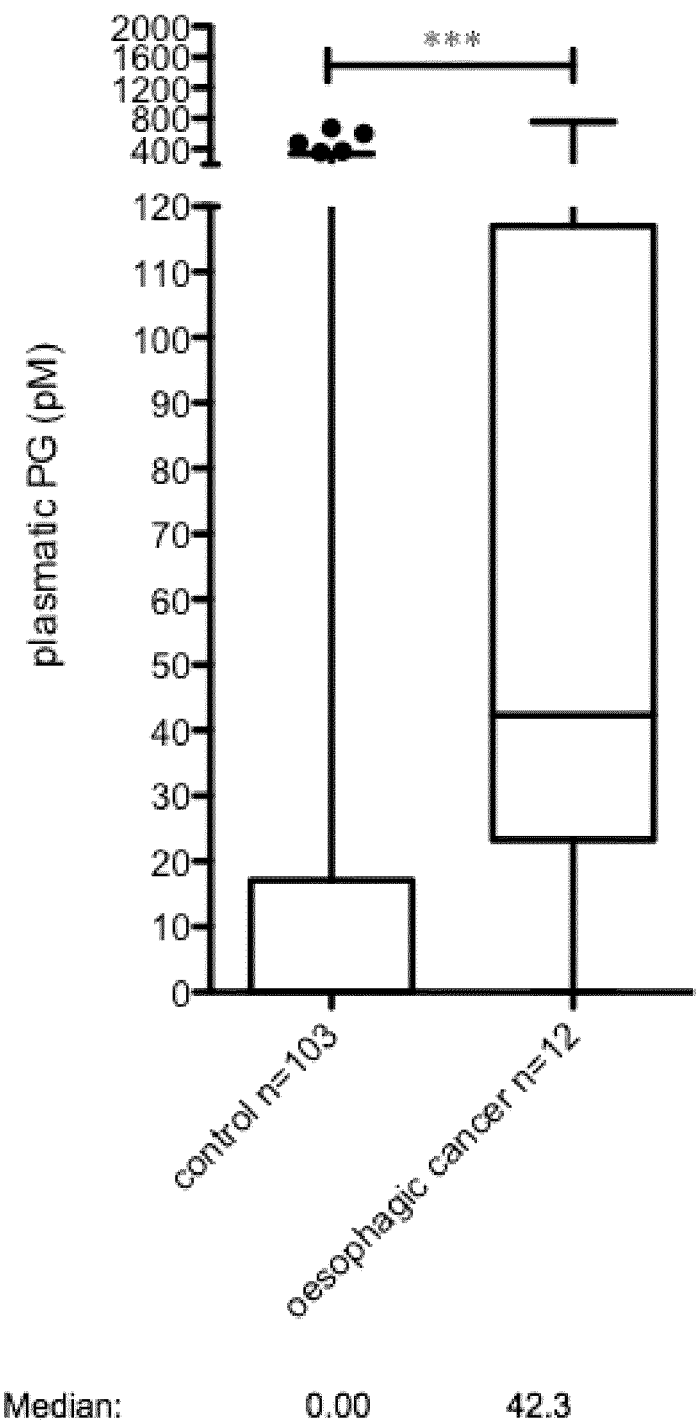

FIG. 6: median plasmatic concentration of progastrin in oesophagic cancer patients (n=12), and in control patients (n=103) using a combination of an N-terminus polyclonal antibody and a C-terminus polyclonal antibody—Mann Whitney test two-tailed, ***p<0.0001

Figure 7:
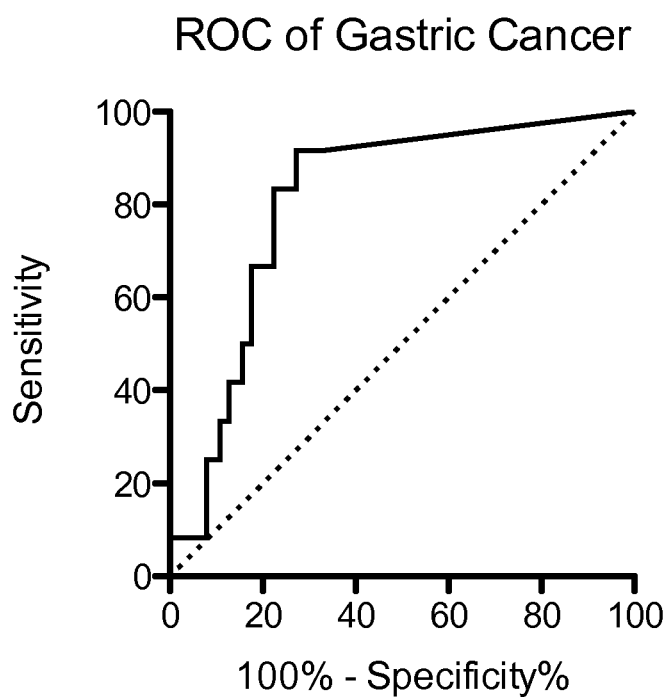

FIG. 7: Receiver operating characteristic (ROC) curve for gastric cancer (upper panel) with the area under the ROC curve and the statistical analysis (lower panel).

Figure 8:
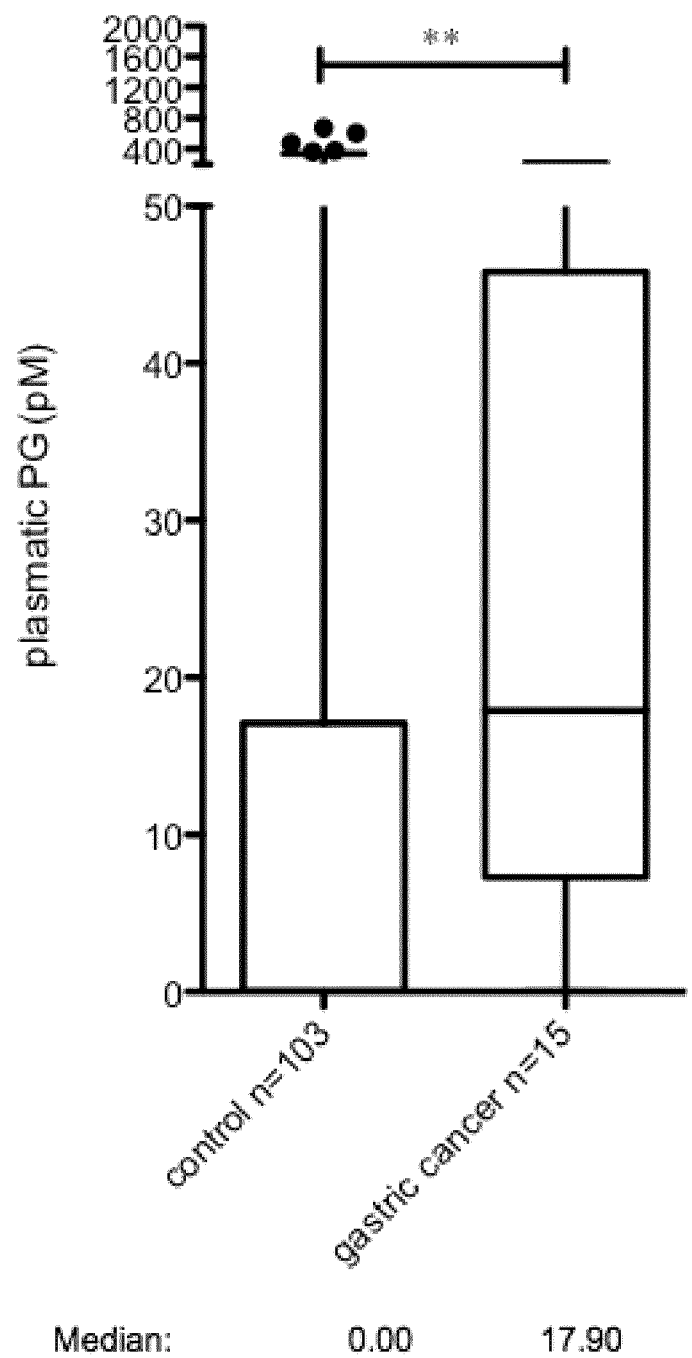

FIG. 8: median plasmatic concentration of progastrin in gastric cancer patients (n=15), and in control patients (n=103) using a combination of an N-terminus polyclonal antibody and a C-terminus polyclonal antibody—Mann Whitney test two-tailed, **p<0.001

Figure 9:
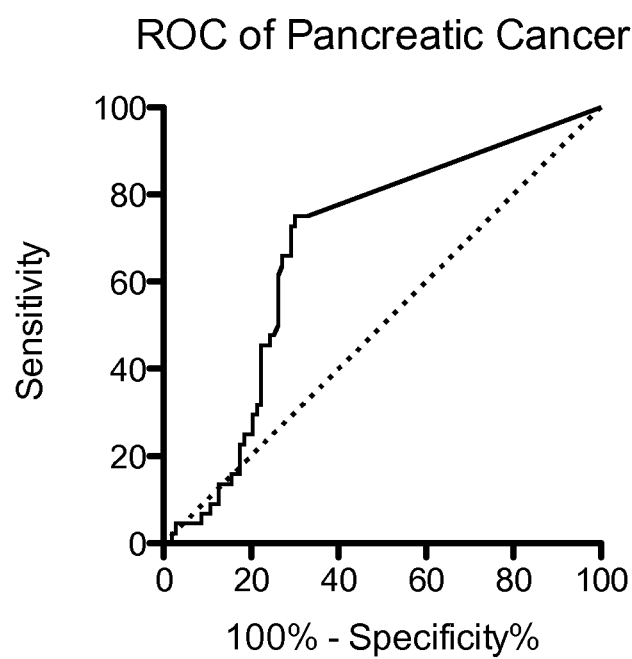

FIG. 9: Receiver operating characteristic (ROC) curve for pancreatic cancer (upper panel) with the area under the ROC curve and the statistical analysis (lower panel).

Figure 10:
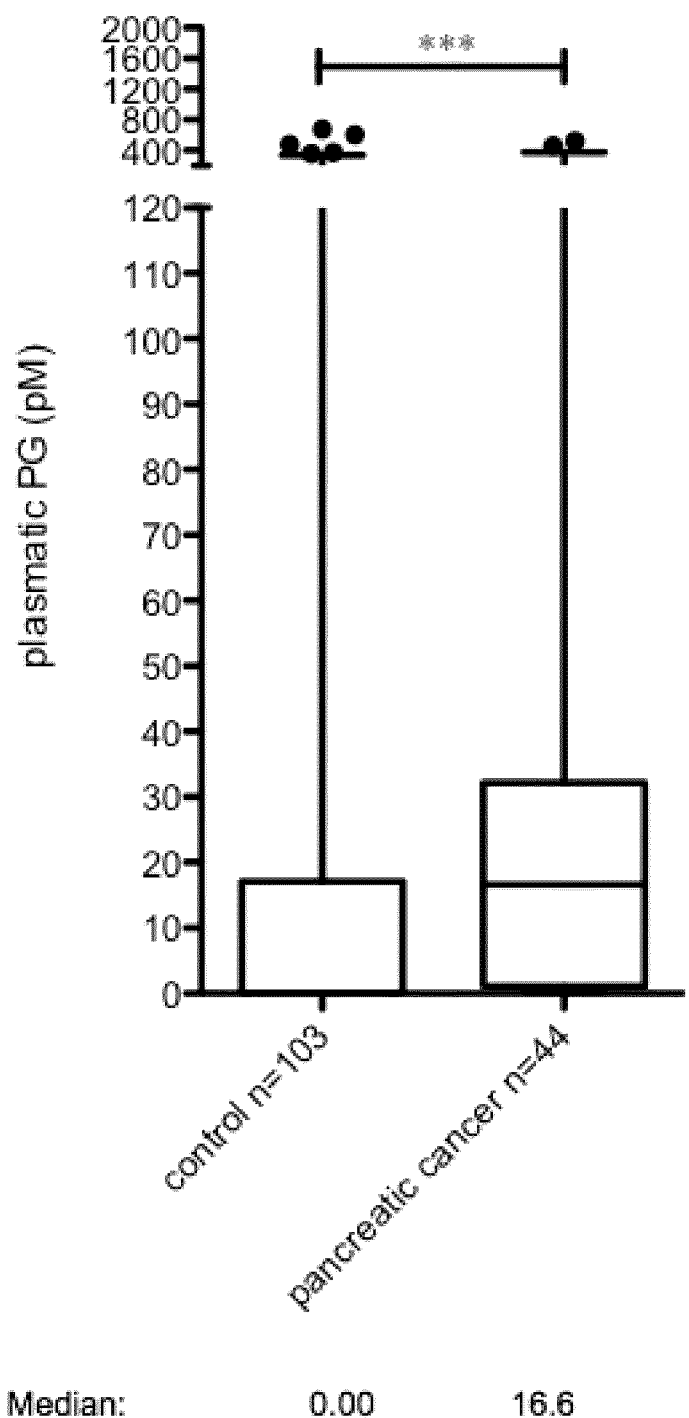

FIG. 10: median plasmatic concentration of progastrin in pancreatic cancer patients (n=44), and in control patients (n=103) using a combination of an N-terminus polyclonal antibody and a C-terminus polyclonal antibody—Mann Whitney test two-tailed, ***p<0.0001

Figure 11:
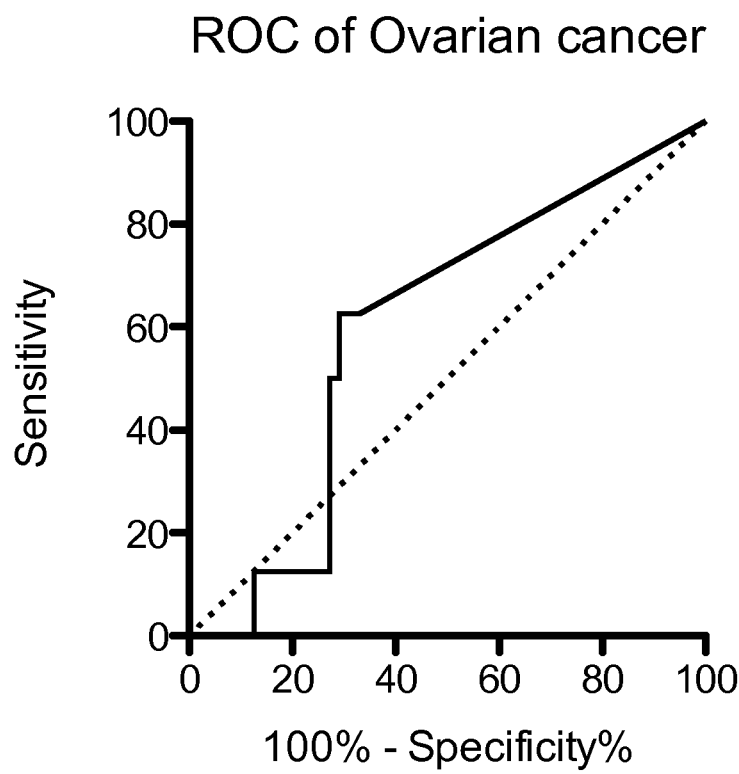

FIG. 11: Receiver operating characteristic (ROC) curve for ovarian cancer (upper panel) with the area under the ROC curve and the statistical analysis (lower panel).

Figure 12:
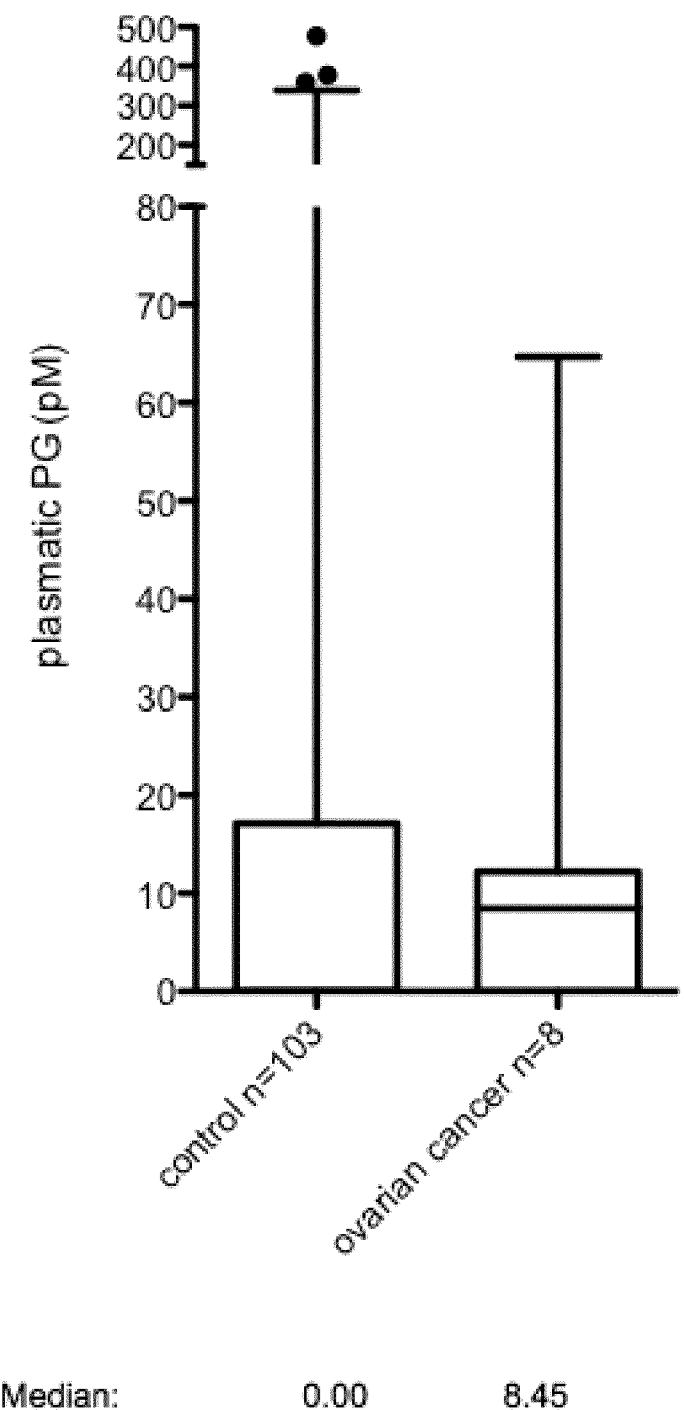

FIG. 12: median plasmatic concentration of progastrin in ovarian cancer patients (n=8), and in control patients (n=103) using a combination of an N-terminus polyclonal antibody and a C-terminus polyclonal antibody.

Figure 14:
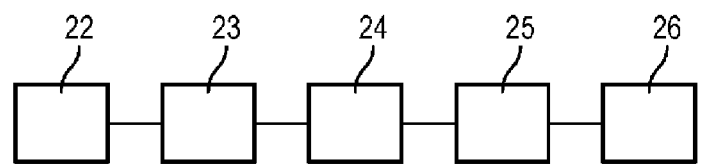

FIG. 13: Schematic representation of a processing system according to a particular embodiment of the present invention FIG. 14: Functional graph representing a method according to a particular embodiment of the present invention.

Figure 15:
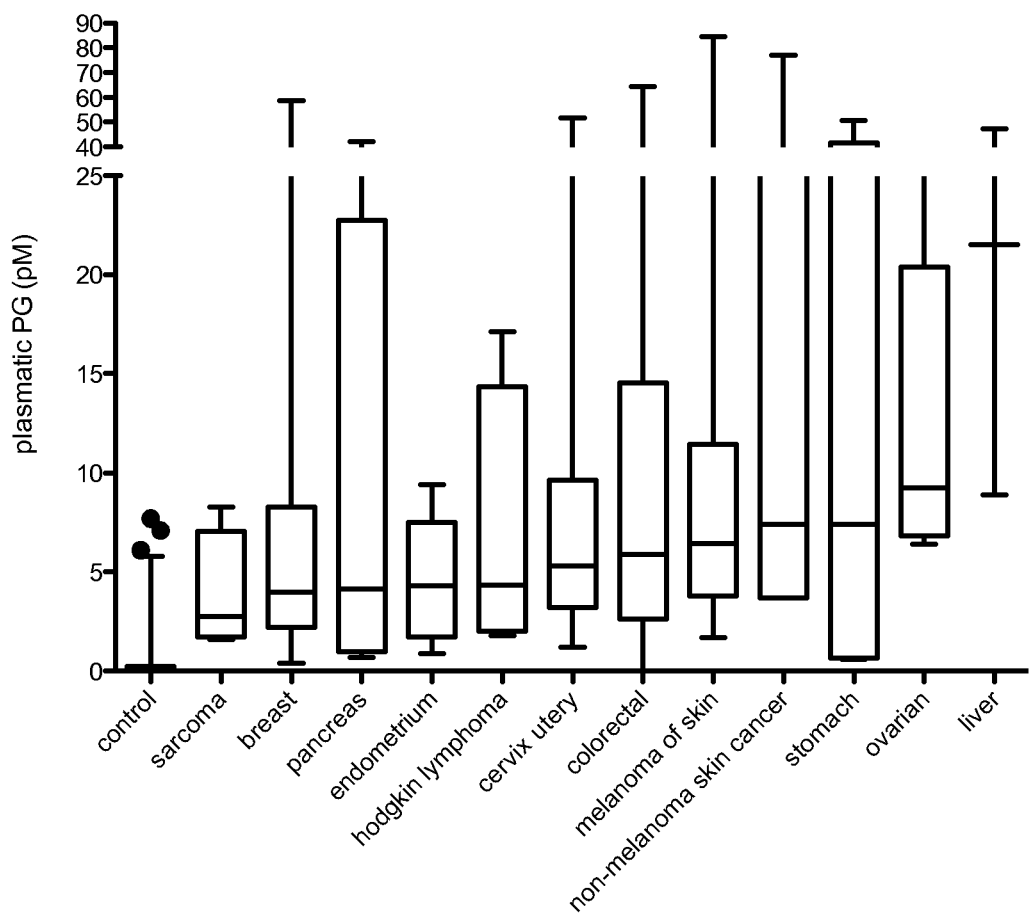

FIG. 15: Median plasmatic concentration of progastrin in various cancer type patients (n=231), and in control patients (n=322) using a combination of a polyclonal antibody and a monoclonal antibody.

Figure 16:
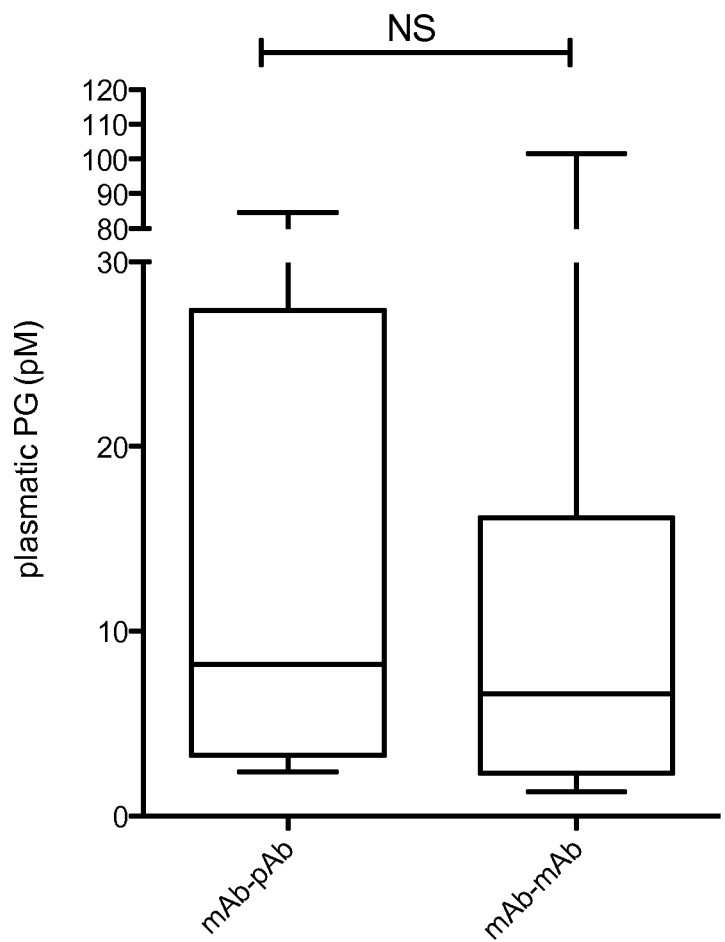

FIG. 16: Median plasmatic concentration of progastrin in various cancer type patients (n=10), using a combination of a polyclonal antibody and monoclonal antibody (mAb-pAb) or a combination of monoclonal antibodies (mAb-mAb)—Mann Whitney test two-tailed, NS p>0.05.

EXAMPLES

Example 1: Detection of Plasmatic Progastrin Concentration Using Polyclonal Antibodies Plasma progastrin levels were quantified by ELISA through the use of two specific anti-progastrin antibodies: capture antibodies are coated on the wells of the plate, whereas revelation antibodies are used to detect progastrin and mediates revelation of the signal.

In the present example, quantification is based on the ELISA method which allows, through the use of a substrate whose reaction emits light, to assign a value proportional to the luminescence amount of antibodies bound to the antigen retained by capture antibodies.

Material

Reagents and apparatus are listed in Table 7:

TABLE 7

| Designation | Provider | Référence |
|---|---|---|
| Plates MaxiSORP white Nunc, 96 wells | Dutscher | # 055221 |
| Sodium Carbonate/Bicarbonate | Sigma | # 21851 |
| DPBS 1X | Lonza | # P04-36500 |
| Tween-20 | Biosolve | # 20452335 |
| BSA | Euromedex | # 04-100-810-C |
| Streptavidin-HRP | Pierce (Thermo) | # 21130 |
| SuperSignal ELISA Femto Maximum Sensitivity Substrate | Pierce (Thermo) | # 37074 |
| Anti-ProGastrin Polyclonal Antibody | Eurogentec | / |

Polyclonal antibodies were obtained by immunizing a rabbit with N-terminal progastrin (SEQ ID N° 2) or with C-terminal progastrin corresponding to amino acids 71 to 80 of hPG and having the sequence FGRRSAEDEN (SEQ ID N° 40), according to standard protocols.

The binding characteristics of polyclonal antibodies against progastrin used in this assay are the following: absence of binding to G34-Gly, G34, G17-Gly, G17, binding to full length progastrin.

96 wells plates are coated by preparing a solution of carbonate—sodium bicarbonate, 50 mM pH 9.6 by dissolving the contents of one capsule in 100 ml of MilliQ water. A solution of capture antibody (3 pg/ml), corresponding to polyclonal antibodies obtained by using the C-terminal of progastrin FGRRSAEDEN (SEQ ID N° 40) is prepared in carbonate buffer. 100 microliters of antibodies solution is added to each well and incubated at 4° C. for 16 hours (1 night). Plates are then blocked by eliminating the antibodies solution and wash 3 times with 300 µl 1×PBS/0.1% Tween-20, then adding 200 µl of blocking buffer (1×PBS/0.1% Tween-20/0.1% BSA) per well, and incubated 2 hours at 22° C. Blocking buffer is then eliminated, wells are washed 3 times with 300 µl 1×PBS/0.1% Tween-20.

Plasma dilution is performed as follows: The plasma is used pure, diluted ½, ⅕ and 1/10. Dilutions are prepared from pure plasma in 1×PBS/0.1% Tween 20/0.1% BSA. For the control test, ELISA in the presence of a known concentration of progastrin, progastrin dilution is prepared as follows: stock recombinant PG (Full length human progastrin produced in *E. coli* and affinity purified with Glutathione agarose/Tag removal (Tev)/IMAC Counter purification/dialysis, from Institut Pasteur, Paris, France) is prepared at a concentration of 0.45 mg/ml (45 microM), in triplicate. Ranges of progastrin concentrations were prepared as follows:

Solution A: Pre-dilution 1/10, 2 µl of stock+18 µl of the buffer
Solution B: Pre-dilution 1/100, 10 µl of A+90 µl of the buffer
Solution C: Pre-dilution 1/1000, 10 µl of B+90 µl of the buffer
Solution D: 500 pM, 5.55 µl of C+494.5 µl of the diluent
Solution E: 250 pM, 250 µl of D+250 µl of the diluent
Solution F: 100 pM, 200 µl of E+300 µl of the diluent
Solution G: 50 pM, 250 µl of F+250 µl of the diluent
Solution H: 25 pM, 200 µl of G+200 µl of the diluent
Solution I: 10 pM, 100 µl of H+150 µl of the diluent The range of recombinant PG is linear and can therefore be more or less extensive according to the antibody used.

For the preparation of test samples, approximately 500 µl of each sample are set aside and stored until analysis (and confirmation if necessary) of the results. 100 µl of each point of the range and/or plasmas are assayed pure, diluted to ½, ⅕ and 1/10, and incubated for 2 hours at 22° C. on the plates.

For the revelation of the test, the plates are washed 3 times with 300 µl 1×PBS/0.1% Tween-20. A solution of the polyclonal rabbit anti-progastrin antibody, wherein said antibodies have been obtained by using the N-terminal part of progastrin as an immunogen, coupled to biotin to 0.5 µg/ml, is prepared by dilution in 1×PBS/0.1% Tween-20/0.1% BSA. 100 µl of this solution is added to each well. Incubation takes place for 1 hour at 22° C. The revelation with streptavidin-HRP is performed by removing detection antibody and wash 3 times with 300 µl 1×PBS/0.1% Tween-20, then preparing a solution of Streptavidin-HRP at 20 ng/ml diluted in 1×PBS/0.1% Tween-20/0.1% BSA, wherein 100 Add 100 µl of this solution is added to each well, before incubation for 1 hour at 22° C.

The detection consists of eliminating streptavidin-HRP and wash 3 times with 300 µl 1×PBS/0.1% Tween-20, then adding 100 µl of chemiluminescent substrate solution per well. The substrate solution is prepared by mixing equal volumes of the two solutions SuperSignal ELISA Femto kit, 20 ml+20 ml, 30 minutes before use and stored at room temperature in the dark. Luminescence is read after 5 minutes incubation at room temperature in the dark.

For each condition, the test is performed in triplicate and the results of the ranges will be presented as a graph showing the change in luminescence depending on the progastrin concentration. For each plasma dilution, the concentration of progastrin is determined using the equation of the linear regression line of the corresponding range (range 1/10th for a sample diluted to 1/10th).

Methods and Results

Progastrin levels were determined in plasma samples from subjects who were known to have developed cancer later. Progastrin was captured with polyclonal antibodies specific for the C-terminus. Detection was performed with labelled polyclonal antibodies specific for the N-terminus.

Importantly, at the time of sample collection, these subjects had never been diagnosed with cancer and did not show any symptom relating to cancer. The control was constituted by plasma samples from the general population.

The results are shown in FIGS. 1-12. The median plasmatic concentration of progastrin was 17 pM in patients who developed colorectal cancer afterwards (n=148), 100 pM in patients who developed hepatocellular carcinoma (n=47), 42.3 pM in patients who developed oesophagic cancer (n=12), 17.90 pM in patients who developed gastric cancer (n=15), 16.6 pM in patients who developed pancreatic cancer (n=44), and 8.45 in patients who developed ovarian cancer (n=8). By comparison, the median plasmatic concentration of progastrin is 0 pM in control subjects (n=103).

These data demonstrate that patients who will develop cancer have detectable levels of progastrin in their plasma whereas healthy control individuals have none. Progastrin can be detected even before any cancer can be diagnosed, making progastrin useful biomarker for the onset of cancer. ROC analysis confirmed the predictive nature of progastrin for each of the above-listed cancers.

These data demonstrate that patients with a risk of developing cancer have higher concentration of progastrin in their plasma compared to healthy control individuals.

Example 2: Detection of Plasmatic Progastrin Concentration Using a Combination of Polyclonal Antibodies and Monoclonal Antibodies In the present example, plasma progastrin levels were quantified by ELISA through the use of antibody specific for human progastrin (hPG) pre-coated on a 96-well plate. Standards and samples are added to the wells, and any hPG present binds to the immobilized capture antibody. The wells are washed and an anti-hPG detection antibody horseradish peroxidase (HRP) conjugate is added, producing an antibody-antigen-antibody "sandwich." After a second wash, TMB substrate solution is added, which produces a blue color in direct proportion to the amount of hPG present in the initial sample. The Stop Solution changes the color from blue to yellow, and the wells are read at 450 nm with a microplate reader.

Polyclonal antibodies were obtained by immunizing a rabbit with N-terminal progastrin (SEQ ID N° 2) or with C-terminal progastrin corresponding to amino acids 71 to 80 of hPG and having the sequence FGRRSAEDEN (SEQ ID N° 40), according to standard protocols.

Monoclonal antibodies were obtained by using hybridomas producing antibodies against N-terminal progastrin (SEQ ID N° 2) or against C-terminal progastrin corresponding to amino acids 71 to 80 of hPG and having the sequence FGRRSAEDEN (SEQ ID N° 40), according to standard protocols.

The binding characteristics of polyclonal and monoclonal antibodies against progastrin used in this assay are the following: absence of binding to G34-Gly, G34, G17-Gly, G17, binding to full length progastrin.

For the control test, ELISA in the presence of a known concentration of progastrin, progastrin dilution is prepared as follows: stock recombinant PG (Full length human progastrin produced in *E. coli* and affinity purified with Glutathione agarose/Tag removal (Tev)/IMAC Counter purification/dialysis, from Institut Pasteur, Paris, France) is prepared at a concentration of 0.45 mg/ml (45 microM), in triplicate. Ranges of progastrin concentrations were prepared as follows:

Solution A: Pre-dilution 1/10, 2 μl of stock+18 μl of the buffer
Solution B: Pre-dilution 1/100, 10 μl of A+90 μl of the buffer
Solution C: Pre-dilution 1/1000, 10 μl of B+90 μl of the buffer
Solution D: 500 pM, 5.55 μl of C+494.5 μl of the diluent
Solution E: 250 pM, 250 μl of D+250 μl of the diluent
Solution F: 100 pM, 200 μl of E+300 μl of the diluent
Solution G: 50 pM, 250 μl of F+250 μl of the diluent
Solution H: 25 pM, 200 μl of G+200 μl of the diluent
Solution I: 10 pM, 100 μl of H+150 μl of the diluent The range of recombinant PG is linear and can therefore be more or less extensive according to the antibody used.
Methods and Results Progastrin levels were determined in plasma samples from subjects who were known to have developed cancer later. Progastrin was captured with the C-terminus monoclonal antibody mAb 14 produced by hybridoma 2H9F4B7 described in WO 2011/083088 (Hybridoma 2H9F4B7 was deposited under the Budapest Treaty at the CNCM, Institut Pasteur, 25-28 rue du Docteur Roux, 75724 Paris CEDEX 15, France, on 27 Dec. 2016, under reference I-5158.). Detection was performed with labelled polyclonal antibodies specific for the N-terminus.

Importantly, at the time of sample collection, these subjects had never been diagnosed with cancer and did not show any symptom relating to cancer. The control was constituted by plasma samples from the general population.

The results are shown in FIG. 15. The median plasmatic concentration of progastrin was ranked between 2.750 and 21.5 pM in patients depending of the type of cancer (n=231). By comparison, the median plasmatic concentration of progastrin is 0 pM in control subjects (n=322).

These data demonstrate that patients who will develop cancer have detectable levels of progastrin in their plasma whereas healthy control individuals have none. Progastrin can be detected even before any cancer can be diagnosed, making progastrin useful biomarker for the onset of cancer.

These data demonstrate that patients with a risk of developing cancer have higher concentration of progastrin in their plasma compared to healthy control individuals.

Example 3: Detection of Plasmatic Progastrin Concentration Using a Combination of Monoclonal Antibodies In the present example, plasma progastrin levels were quantified by ELISA through the use of antibody specific for human progastrin (hPG) pre-coated on a 96-well plate. Standards and samples are added to the wells, and any hPG present binds to the immobilized capture antibody. The wells are washed and an anti-hPG detection antibody horseradish peroxidase (HRP) conjugate is added, producing an antibody-antigen-antibody "sandwich." After a second wash, TMB substrate solution is added, which produces a blue color in direct proportion to the amount of hPG present in the initial sample. The Stop Solution changes the color from blue to yellow, and the wells are read at 450 nm with a microplate reader.

Polyclonal antibodies were obtained by immunizing a rabbit with N-terminal progastrin (SEQ ID N° 2) or with C-terminal progastrin corresponding to amino acids 71 to 80 of hPG and having the sequence FGRRSAEDEN (SEQ ID N° 40), according to standard protocols.

Monoclonal antibodies were obtained by using hybridomas producing antibodies against N-terminal progastrin (SEQ ID N° 2) or against C-terminal progastrin corresponding to amino acids 71 to 80 of hPG and having the sequence FGRRSAEDEN (SEQ ID N° 40), according to standard protocols.

The binding characteristics of polyclonal and monoclonal antibodies against progastrin used in this assay are the following: absence of binding to G34-Gly, G34, G17-Gly, G17, binding to full length progastrin.

For the control test, ELISA in the presence of a known concentration of progastrin, progastrin dilution is prepared as follows: stock recombinant PG (Full length human progastrin produced in *E. coli* and affinity purified with Glutathione agarose/Tag removal (Tev)/IMAC Counter purification/dialysis, from Institut Pasteur, Paris, France) is prepared at a concentration of 0.45 mg/ml (45 microM), in triplicate. Ranges of progastrin concentrations were prepared as follows:

Solution A: Pre-dilution 1/10, 2 μl of stock+18 μl of the buffer
Solution B: Pre-dilution 1/100, 10 μl of A+90 μl of the buffer
Solution C: Pre-dilution 1/1000, 10 μl of B+90 μl of the buffer
Solution D: 500 pM, 5.55 μl of C+494.5 μl of the diluent
Solution E: 250 pM, 250 μl of D+250 μl of the diluent Solution F: 100 pM, 200 µl of E+300 µl of the diluent
Solution G: 50 pM, 250 µl of F+250 µl of the diluent
Solution H: 25 pM, 200 µl of G+200 µl of the diluent
Solution I: 10 pM, 100 µl of H+150 µl of the diluent The range of recombinant PG is linear and can therefore be more or less extensive according to the antibody used.

Methods and Results

Progastrin levels were determined in plasma samples from subjects who were known to have developed cancer later. Progastrin was captured with the C-terminus monoclonal antibody mAb 14 produced by hybridoma 2H9F4B7 described in WO 2011/083088 (Hybridoma 2H9F4B7 was deposited under the Budapest Treaty at the CNCM, Institut Pasteur, 25-28 rue du Docteur Roux, 75724 Paris CEDEX 15, France, on 27 Dec. 2016, under reference I-5158.). Detection was performed with labelled monoclonal antibody mAb 16 described in WO 2011/083088 which is specific for the N-terminus.

Importantly, at the time of sample collection, these subjects had never been diagnosed with cancer and did not show any symptom relating to cancer. The control was constituted by plasma samples from the general population.

The results are shown in FIG. 16. The median plasmatic concentration of progastrin using mAb-pAb et mAb-mAb were similar in median (8.2 vs 6.6 pM respectively) and mean (18.99 vs 16.79 pM) respectively (n=10).

These data demonstrate that mAb-pAb and mAb-mAb ELISA sandwich tests detect both progastrin in the plasma of patients. Importantly, no significant difference between both tests could be identified. In particular, the sensitivity of the mAb-pAb and mAb-mAb sandwiches were highly similar. Therefore mAb-mAb ELISA sandwich can be used reliably to detect progastrin in the plasma of patient even before any cancer can be diagnosed, making progastrin useful biomarker for the onset of cancer.

These data demonstrate that patients with a risk of developing cancer have higher concentration of progastrin in their plasma compared to healthy control individuals.

The invention claimed is:

1. A kit comprising at least one anti-progastrin antibody for evaluating risks of developing cancer in a subject who has not been previously diagnosed with cancer, wherein the anti-progastrin antibody is a monoclonal antibody produced by the hybridoma deposited at the CNCM, Institut Pasteur, 25-28 rue du Docteur Roux, 75724 Paris CEDEX 15, France, on 27 Dec. 2016, under reference I-5158.

2. A kit for evaluating risks of developing cancer in a subject who has not been previously diagnosed with cancer, comprising:
   (i) a first anti-progastrin antibody which binds to a first part of progastrin, wherein the anti-progastrin antibody is a monoclonal antibody produced by the hybridoma deposited at the CNCM, Institut Pasteur, 25-28 rue du Docteur Roux, 75724 Paris CEDEX 15, France, on 27 Dec. 2016, under reference I-5158, and
   (ii) a second anti-progastrin antibody which binds to a second part of progastrin.

3. The kit of claim 2, wherein the second anti-progastrin antibody is:
   a monoclonal antibody comprising:
      a heavy chain comprising the following three heavy chain complementarity determining regions ("CDR-H"), CDR-H1, CDR-H2 and CDR-H3 of amino acid sequences SEQ ID NO:16, SEQ ID NO:17, and SEQ ID NO:18, respectively, and
      a light chain comprising the following three light chain complementarity determining regions ("CDR-L"), CDR-L1, CDR-L2 and CDR-L3 of amino acid sequences SEQ ID NO:19, SEQ ID NO:20, and SEQ ID NO:21, respectively.

* * * * *